US011623068B2

(12) United States Patent
Sarabia

(10) Patent No.: US 11,623,068 B2
(45) Date of Patent: Apr. 11, 2023

(54) STEERABLE INTRODUCER SHEATH ASSEMBLY

(71) Applicant: Keystone Heart Ltd., Caesarea (IL)

(72) Inventor: Jaime Eduardo Sarabia, Mableton, GA (US)

(73) Assignee: Kesytone Heart Ltd., Caesarea (IL)

( * ) Notice: Subject to any disclaimer, the term of this patent is extended or adjusted under 35 U.S.C. 154(b) by 164 days.

(21) Appl. No.: 16/968,847

(22) PCT Filed: Feb. 8, 2019

(86) PCT No.: PCT/US2019/017243
§ 371 (c)(1),
(2) Date: Aug. 10, 2020

(87) PCT Pub. No.: WO2019/157303
PCT Pub. Date: Aug. 15, 2019

(65) Prior Publication Data
US 2021/0016062 A1     Jan. 21, 2021

(30) Foreign Application Priority Data

Feb. 12, 2018  (CN) .......................... 201810146156.9
Feb. 12, 2018  (CN) .......................... 201820252716.4

(51) Int. Cl.
*A61M 25/01*     (2006.01)
*A61M 25/06*     (2006.01)
(Continued)

(52) U.S. Cl.
CPC .... *A61M 25/0136* (2013.01); *A61M 25/0147* (2013.01); *A61M 25/0662* (2013.01); *A61M 29/00* (2013.01); *A61M 2025/0036* (2013.01)

(58) Field of Classification Search
CPC .......... A61M 25/0062; A61M 25/0136; A61M 25/0147; A61B 2034/301; A61B 2017/003; A61B 2017/00318
See application file for complete search history.

(56) References Cited

U.S. PATENT DOCUMENTS 5,273,535 A * 12/1993 Edwards ........... A61M 25/0138
                                                      604/95.01
5,325,845 A *  7/1994 Adair .................... A61B 1/0055
                                                      604/95.04
(Continued)

FOREIGN PATENT DOCUMENTS

CN     103181819 A     7/2013
CN     105188827 A    12/2015
(Continued)

OTHER PUBLICATIONS

European Patent Office, Extended European Search Report dated Jul. 26, 2021 in European Patent Application No. 21160723.9, 6 pages.
(Continued)

*Primary Examiner* — Laura A Bouchelle
(74) *Attorney, Agent, or Firm* — Inskeep IP Group, Inc.

(57) ABSTRACT

An introducer sheath assembly having a handle portion including a distal end and a proximal end, and an introducer sheath extending outwardly from the distal end of the handle portion, the introducer sheath including a device lumen configured to slidably receive a corresponding device, a guidewire lumen configured to slidably receive a corresponding guidewire, and at least one steering cable disposed within at least one steering cable lumens that are disposed radially outwardly from the device lumen, and the handle portion including at least one steering assembly for modifying the tension of at least one of the at least one steering cables.

17 Claims, 32 Drawing Sheets

(51) Int. Cl.
*A61M 29/00* (2006.01)
*A61M 25/00* (2006.01)

(56) References Cited

U.S. PATENT DOCUMENTS

| | | | | |
|---|---|---|---|---|
| 5,399,164 | A * | 3/1995 | Snoke | A61M 25/0136 |
| | | | | 604/524 |
| 8,808,345 | B2 * | 8/2014 | Clark | A61B 34/74 |
| | | | | 607/113 |
| 2001/0037051 | A1 | 11/2001 | Fujii et al. | |
| 2003/0236493 | A1 | 12/2003 | Mauch | |
| 2007/0260225 | A1 | 11/2007 | Sakakine et al. | |
| 2009/0287188 | A1 | 11/2009 | Golden et al. | |
| 2014/0336573 | A1 | 11/2014 | Yu et al. | |
| 2016/0193449 | A1 * | 7/2016 | Sarabia | A61M 25/0136 |
| | | | | 604/95.04 |

FOREIGN PATENT DOCUMENTS

| | | | |
|---|---|---|---|
| EP | 2609886 A2 | 7/2013 | |
| EP | 3187222 A1 | 7/2017 | |
| WO | WO 2016/178705 A1 | 11/2016 | |

OTHER PUBLICATIONS

WIPO, European International Search Authority, International Search Report and Written Opinion dated Jul. 15, 2019 in International Patent Application No. PCT/US2019/017243, 26 pages.

China Patent Office, Office Action dated Feb. 22, 2022 with English translation in Chinese Patent Application No. 2019800128542, 15 pages.

* cited by examiner

STEERABLE INTRODUCER SHEATH ASSEMBLY

CROSS REFERENCE TO RELATED APPLICATIONS

This application is the U.S. National Phase of and claims priority to International Patent Application No. PCT/US2019/017243, International Filing Date Feb. 8, 2019, entitled Improved Steerable Introducer Sheath Assembly; which claims the benefit of priority of Chinese invention patent application no. 201810146156.9, filed on Feb. 12, 2018, and claims the benefit of priority of Chinese utility model application no. 201820252716.4, filed on Feb. 12, 2018. The foregoing applications are incorporated herein by reference in their entirety entireties.

FIELD OF THE INVENTION

The present disclosure relates generally to medical devices and, more specifically, to vascular access sheaths and catheters.

BACKGROUND OF THE INVENTION

Increasingly, minimally-invasive, catheter-based therapies are being developed that allow physicians to provide therapies to patients whose existing comorbidities may preclude them from having a needed, but more invasive, surgical procedure. Over the last 30-plus years, catheter-based procedures that involve puncturing/crossing the interatrial septum, such as cardiac ablation and balloon valvuloplasty have become commonplace. In the last 5 to 10 years, new structural heart procedures, such as transcatheter valve repair/replacement, and left atrial appendage occlusion, have gained regulatory approvals and have become increasingly common procedures performed in the cardiac catheterization laboratory or hybrid operating room. With the advent of these technologies has come an increase in the need for structural heart interventionalists (specialty physicians who perform these types of procedures) to engage and cross the interatrial septum in the heart.

Historically, crossing the septum has been the purview of pediatric cardiologists or electrophysiologists due to the prevalence of cardiac ablation procedures which require crossing the interatrial septum. However, interventional cardiologists are increasingly starting to provide therapy to the left side of the heart and the requirement to puncture the interatrial septum and provide these new therapies is increasing. Unfortunately, many of these interventional cardiologists do not perform a transseptal puncture with enough regularity to become proficient at it. For these left-sided procedures, safely puncturing the interatrial septum and gaining access to the left side of the heart is not enough. These new technologies demand a very specific and safe location when crossing the interatrial septum. Additionally, crossing the interatrial septum has been historically guided by fluoroscopy (X-ray), and more recently by echocardiographic ultrasound (intracardiac echocardiography, transesophageal echocardiography or transthoracic echocardiography). Fluoroscopy is limited in its role due to its limited ability to image soft tissue, such as the interatrial septum. Therefore, echocardiography is increasingly being relied upon to guide these types of procedures.

As such, it is desirable to provide these newly evolving structural heart interventionalists with a tool to help them safely and accurately cross the interatrial septum. Preferably, these tools may have features that facilitate the accurate positioning of vascular sheaths, catheters, and other instruments used for catheter-based therapies, including transseptal procedures. Such tools may also include features that may increase their utility with echocardiographic imaging, and may enhance the echocardiographic information or facilitate certain modalities of echocardiography to be used for image guidance that might not otherwise be useful.

The present invention recognizes and addresses considerations of prior art constructions and methods.

SUMMARY OF THE INVENTION

An introducer sheath assembly, characterized by a handle portion including a distal end and a proximal end; an introducer sheath extending outwardly from the distal end of the handle portion, the introducer sheath including a device lumen configured to slidably receive a corresponding device, a first steering cable lumen, a second steering cable lumen, and a third steering cable lumen, and a first steering cable affixed at a distal end of the introducer sheath and disposed in the first steering cable lumen, a second steering cable affixed at a distal end of the introducer sheath and disposed in the second steering cable lumen, and a third steering cable affixed at a distal end of the introducer sheath and disposed in the third steering cable lumen, wherein the first, second, and third steering cable lumens are disposed radially outwardly from the device lumen, with the first and second steering cable lumens situated on opposite sides of a vertical plane running through the device lumen and the third cable lumen; a first steering assembly disposed in the handle portion that comprises an element to which a proximal end of the first steering cable is attached, and an element to which a proximal end of the second steering cable is attached; a first steering lever disposed on an outer surface of the handle portion and affixed to a first end of a first steering post, with said first steering post having a second end that engages the first steering assembly such that rotating the steering lever about the longitudinal axis of the first steering post causes the first steering assembly to simultaneously modify the tension in the first and second steering cables; a second steering assembly disposed in the handle portion to which a proximal end of the third steering cable is attached; and a second steering lever disposed on an outer surface of the handle portion and affixed to a first end of a second steering post, with said second steering post having a second end that engages with the second steering assembly such that rotating the steering lever about the longitudinal axis of the second steering post causes the second steering assembly modify the tension in the third steering cable.

Another embodiment of an introducer sheath assembly in accordance with the present disclosure includes a handle portion having a distal end and a proximal end; an introducer sheath extending outwardly from the distal end of the handle portion, the introducer sheath including, a device lumen configured to slidably receive a corresponding device, a first steering cable lumen, a second steering cable lumen, and a third steering cable lumen, and a first steering cable affixed at a distal end of the introducer sheath and disposed in the first steering cable lumen, a second steering cable affixed at a distal end of the introducer sheath and disposed in the second steering cable lumen, a third steering cable affixed at a distal end of the introducer sheath and disposed in the third steering cable lumen, and a fourth steering cable affixed at a distal end of the introducer sheath and disposed in the fourth steering cable lumen, wherein the first, second, third, and fourth steering cable lumens are disposed radially outwardly from the device lumen, with the first and second steering cable lumens situated on opposite sides of a vertical plane in which a longitudinal center axis of the introducer sheath lies, and the third and fourth steering cable lumens situated on opposite sides of a horizontal plane in which a longitudinal center axis of the introducer sheath lies; a first steering assembly disposed in the handle portion that comprises an element to which a proximal end of the first steering cable is attached, and an element to which a proximal end of the second steering cable is attached; and a second steering assembly disposed in the handle portion that comprises an element to which a proximal end of the third steering cable is attached, and an element to which a proximal end of the fourth steering cable is attached; wherein the first steering assembly can be manipulated to simultaneously modify the tension in the first and second steering cables, and the second steering assembly can be manipulated to simultaneously modify the tension in the third and fourth steering cables.

Another embodiment of an introducer sheath assembly in accordance with the present disclosure includes a handle portion having a distal end and a proximal end; an introducer sheath extending outwardly from the distal end of the handle portion, the introducer sheath including, a device lumen configured to slidably receive a corresponding device, at least one steering cable lumen disposed radially outwardly from the device lumen, at least one steering cable that is affixed at a distal end of the introducer sheath, disposed within the at least one steering cable lumen, and engaged with a steering assembly disposed in the handle portion; one or more steering levers disposed on an outer surface of the handle portion and affixed to a first end of a steering post, with said steering post having a second end that engages a steering assembly such that rotating the steering lever about the longitudinal axis of the steering post causes the steering assembly to modify the tension in the at least one steering cable; and wherein at least one steering lever engages either directly or indirectly with the surface of the handle portion in a manner that limits the extent to which the steering lever can be rotated about the longitudinal axis of the steering post.

Another embodiment of an introducer sheath assembly in accordance with the present disclosure includes a handle portion having a distal end and a proximal end; an introducer sheath extending outwardly from the distal end of the handle portion, the introducer sheath including, a device lumen configured to slidably receive a corresponding device, at least one steering cable lumen disposed radially outwardly from the device lumen, at least one steering cable that is affixed at a distal end of the introducer sheath, disposed within the at least one steering cable lumen, and engaged with a steering assembly disposed in the handle portion; one or more steering levers disposed on an outer surface of the handle portion and affixed to a first end of a steering post, with said steering post having a second end that engages a steering assembly such that rotating the steering lever about the longitudinal axis of the steering post causes the steering assembly to modify the tension in the at least one steering cable; and is wherein the engagement between at least one steering lever and the outer surface of the handle portion is mediated by a domed cap that at least partially encompasses the steering lever, with said domed cap being seated in a corresponding-shaped recess in the outer surface of the handle.

Another embodiment of an introducer sheath assembly in accordance with the present disclosure includes a handle portion having a distal end and a proximal end; an introducer sheath extending outwardly from the distal end of the handle portion, the introducer sheath including, a device lumen configured to slidably receive a corresponding device, at least two steering cable lumens disposed radially outwardly from the device lumen, at least two steering cables that are affixed at a distal end of the introducer sheath, and disposed within the at least two steering cable lumens; a first steering assembly disposed in the handle portion that comprises an element to which a proximal end of at least one steering cable is of the at least two steering cables attached; and a second steering assembly disposed in the handle portion that comprises an element to which a proximal end of at least one steering cable of the at least two steering cables is attached; wherein the first steering assembly can be manipulated to modify the tension in the steering cables attached to it, and the second steering assembly can be manipulated modify the tension in the steering cables attached to it; and a slack removal assembly that acts to remove excess slack from at least one of the steering cables attached to at least one of the steering assemblies when the other steering assembly is manipulated to modify the tension in at least one of its attached steering cables.

Another embodiment of an introducer sheath assembly in accordance with the present disclosure includes a handle portion having a distal end and a proximal end; an introducer sheath extending outwardly from the distal end of the handle portion, the introducer sheath including a device lumen configured to slidably receive a corresponding device; a device locking assembly disposed at the rear end of the housing portion comprising a device locking stem defining an axially extending bore that is confirmed to slidably receive the corresponding device, the device locking stem being axially movable with respect to the handle portion, a clamp disposed on the device locking stem, the clamp being selectively positioned in a locked position in which the corresponding device is axially fixed with respect to the device locking stem, and an unlocked position in which the corresponding device is slidable within the axially extending bore of the device locking stem, wherein the device locking assembly further comprises an advance knob that is both axially fixed and rotatable with respect to the handle portion of the body portion, with said advance knob further comprising a threaded bore that is correspondingly threaded to an outer surface of the device locking stem, the said device locking stem being threadably engaged with the threaded bore of the advance knob; and wherein the device locking stem further engages with a stem guide that is seated within the handle portion in such a way as to prevent the locking stem from rotating when the rotating knob is rotated. Such an embodiment may also include features to facilitate injection molding manufacturing techniques, including parallel, interrupting flats in the external threads on the outer surface of the device locking stem, and an advance knob that is further characterized by outwardly depending members that together define a discontinuous radial flange with a radius that is greater than that of a distal aperture in the handle portion, with said discontinuous radial flange permitting advance knob to be rotatably seated and retained within said distal aperture in the handle portion, with said flanges mirrored by openings that pass through the advance knob.

Another embodiment of an introducer sheath assembly in accordance with the present disclosure includes a handle portion having a distal end and a proximal end; an introducer sheath extending outwardly from the distal end of the handle portion, the introducer sheath including, a device lumen configured to slidably receive a corresponding device, at least one steering cable lumen disposed radially outwardly from the device lumen, at least one steering cable that is affixed at a distal end of the introducer sheath, disposed within the at least one steering cable lumen, and engaged with a steering assembly disposed in the handle portion, with said steering assembly capable of modifying the tension in the at least one steering cable; and a torque transmission lock that prevents the introducer sheath from rotating about longitudinal center axis when said steering assembly is used to modify the tension in the at least one steering cable. The torque transmission lock may further comprise a hollow column with an internal diameter sufficient to encompass the radial diameter the introducer sheath, and at least one proximal structure that is capable of engaging with at least one corresponding structure extending from a face of the handle portion.

Another embodiment of an introducer sheath assembly in accordance with the present disclosure includes a handle portion having a distal end and a proximal end; an introducer sheath extending outwardly from the distal end of the handle portion, the introducer sheath including a device lumen configured to slidably receive a corresponding device; and an aperture in the handle portion that allows a user to visualize the point at which the corresponding device has been received into the device lumen of the introducer sheath, and may further comprise a corresponding device containing markings that can be visualized through the aperture to provide the user with an indication of the extent to which the corresponding device has been inserted into the device lumen of the introducer sheath.

A further embodiment of an introducer sheath assembly in accordance with the present disclosure includes a handle portion having a distal end and a proximal end; an introducer sheath extending outwardly from the distal end of the handle portion, the introducer sheath including a device lumen configured to slidably receive a corresponding device; wherein the corresponding device includes one or more modifications that improve ultrasonic visualization. In certain such embodiments, the corresponding device is a dilator with a hollow axial bore that contains modifications that improve ultrasonic visualization that are located on an internal surface of the hollow axial bore. For example, such a dilator may include at least one linear groove that extends in a parallel fashion with respect to the longitudinal center axis of the dilator, and by way of further example may include at least one linear groove having a width of about 0.012 inches, and a depth of up to about 0.003 inches, with said grooves in certain embodiments having a total length of about 0.375 inches, and in certain further embodiments being comprised of continuous steps with a length of about 0.0625 inches.

BRIEF DESCRIPTION OF THE DRAWINGS

The accompanying drawings, which are incorporated in and constitute a part of this specification, illustrate one or more embodiments of the invention and, together with the description, serve to explain the principles of the invention.

A full and enabling disclosure of the present invention, including the best mode thereof, directed to one of ordinary skill in the art, is set forth in the specification, which makes reference to the appended drawings, in which.

Figure 1A:
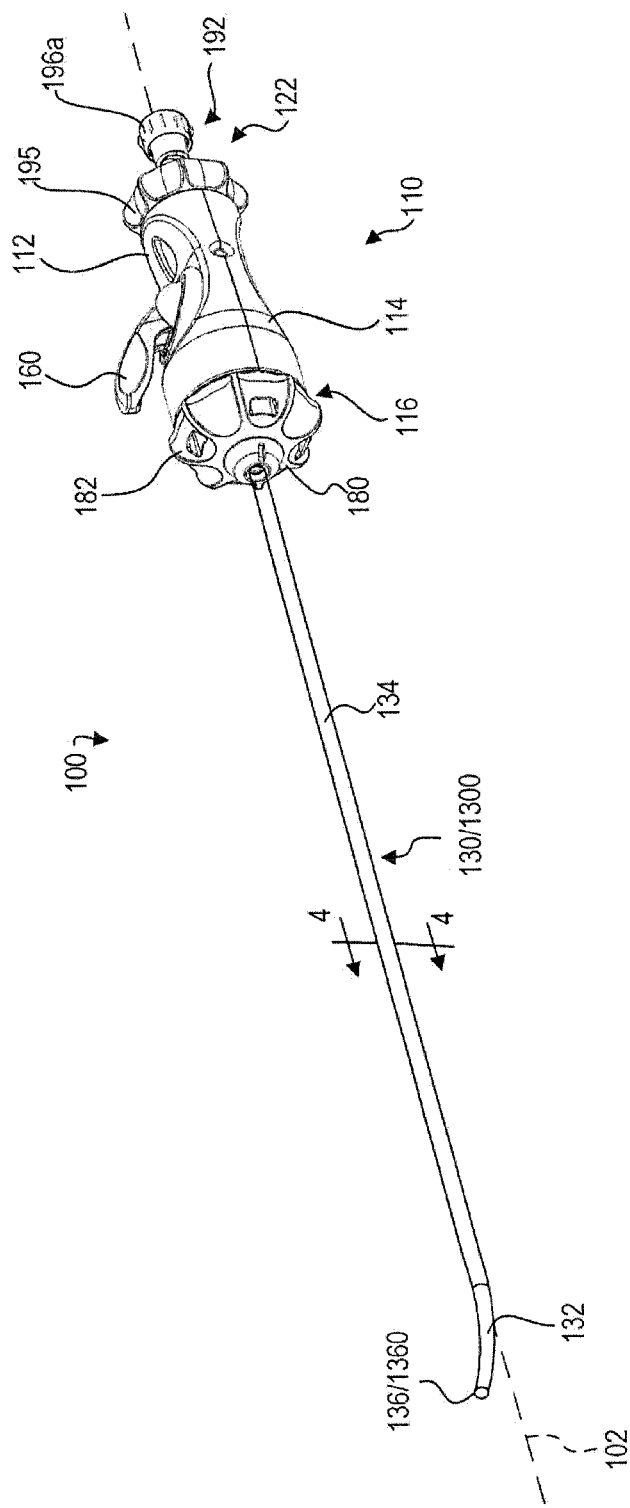
FIG. 1A is a top perspective view of a steerable introducer sheath assembly in accordance with an embodiment of the present disclosure.

Repeated use of reference characters in the present specification and drawings is intended to represent same or analogous features or elements of the invention according to the disclosure.

DETAILED DESCRIPTION

Reference will now be made in detail to certain embodiments of the present invention, examples of which are illustrated in the accompanying Figures. These embodiments are provided by way of example, and should not be construed as limiting the scope of the claimed invention to any particular embodiment. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the recited claims and their equivalents.

In the descriptions of steerable introducer sheath embodiments that are provided herein, the terms "distal" and "proximal" will be used to describe both movement and relative position. As can be seen in FIGS. 1A-1D, the term "distal" signifies relative position and/or movement in the direction of terminal end 136 of introducer sheath 130 (i.e., in the direction of the patient), and "proximal" signifies relative position and/or movement in the direction of device lock assembly 192 (i.e., in the direction of the user).

In the descriptions within, the term "about" should be interpreted as +/−10%.

Figure 8A:
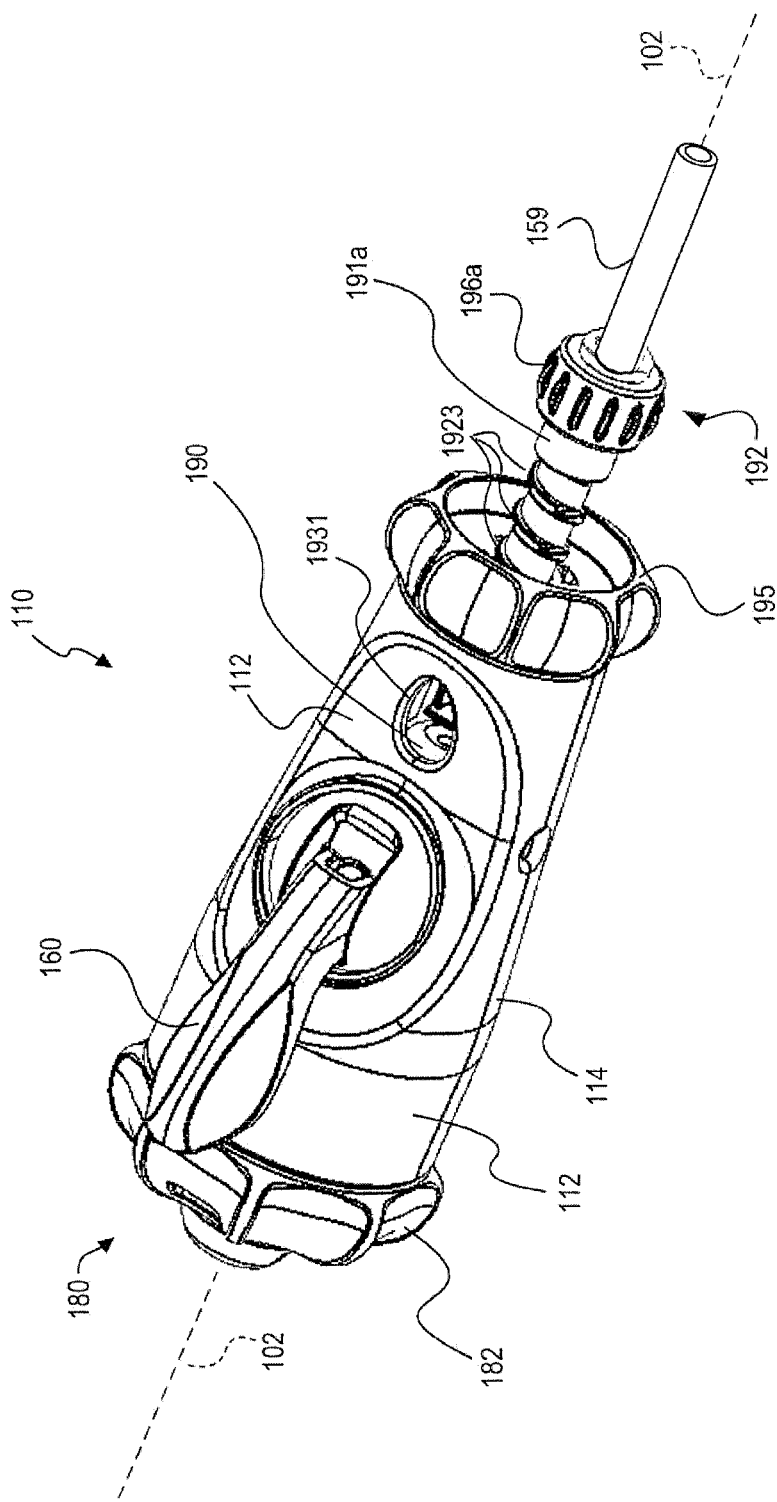
FIG. 8A is a top perspective view of the handle portion of a steerable introducer sheath assembly in accordance with an embodiment of the present disclosure.
Figure 8B:
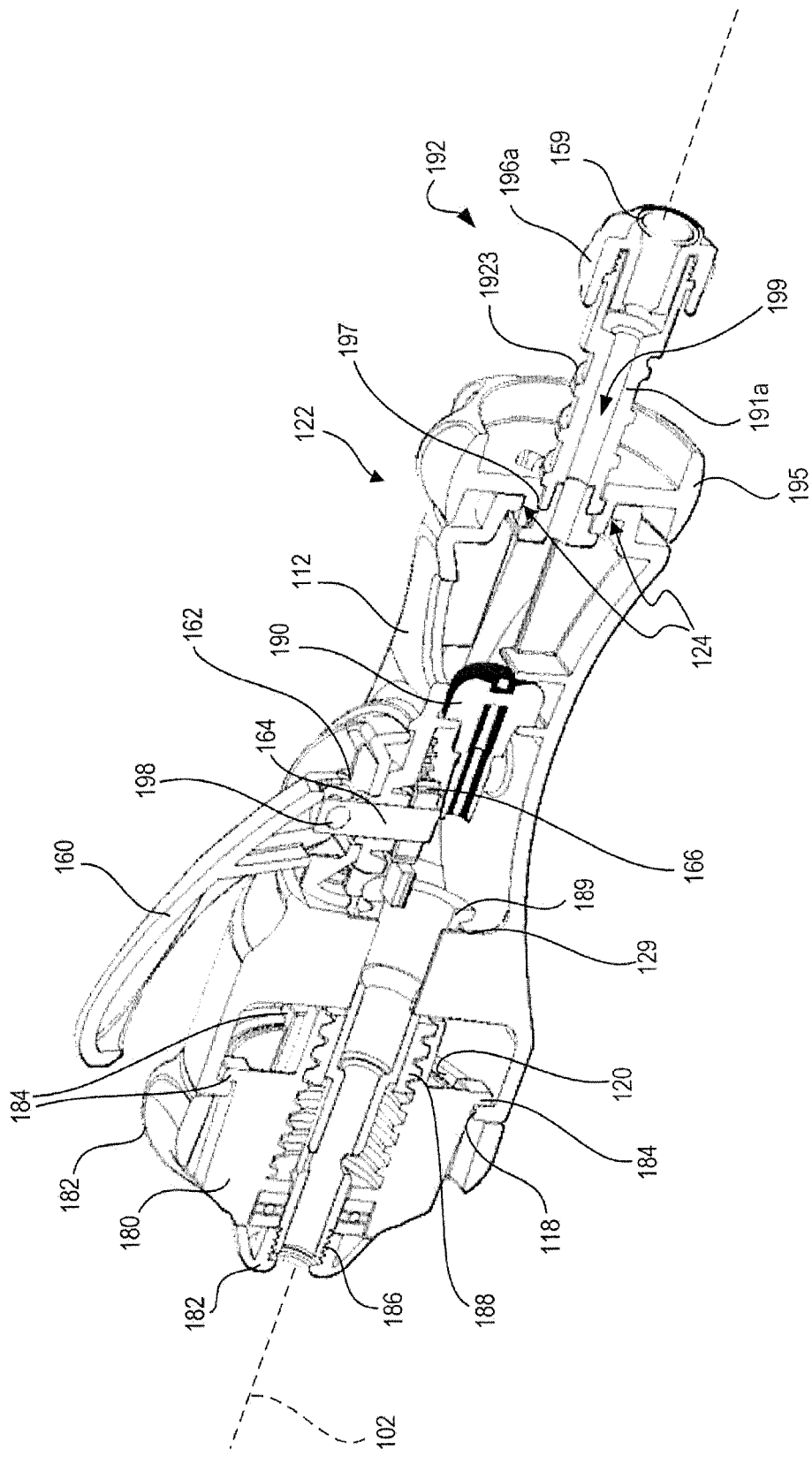
FIG. 8B is a side-perspective, cross-sectional view of the handle portion of a steerable introducer sheath assembly in accordance with an embodiment of the present disclosure.
Figure 8C:
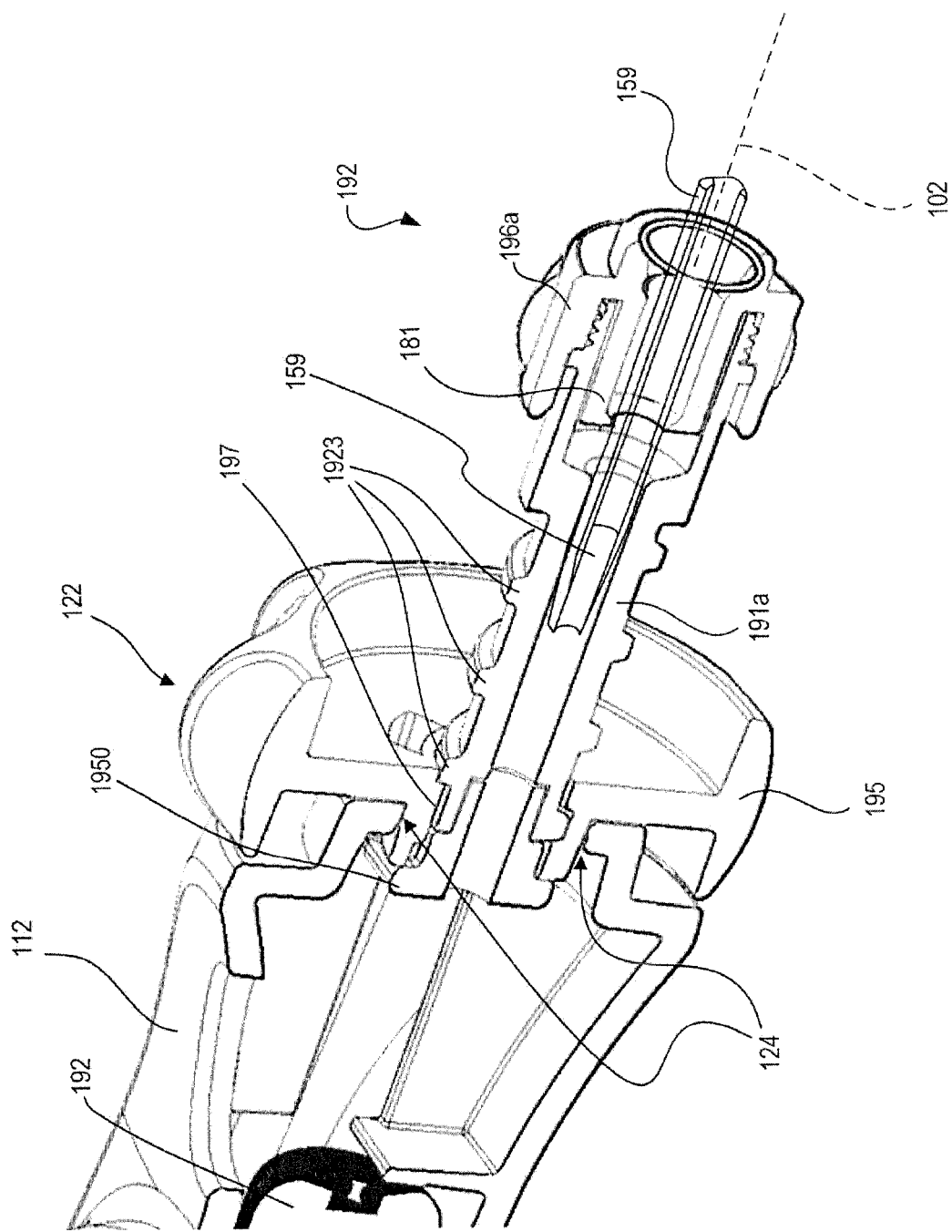
FIG. 8C is a side-perspective, cross-sectional view of the proximal end of the handle portion of the steerable introducer sheath assembly shown in FIG. 8B.
Figure 8D:
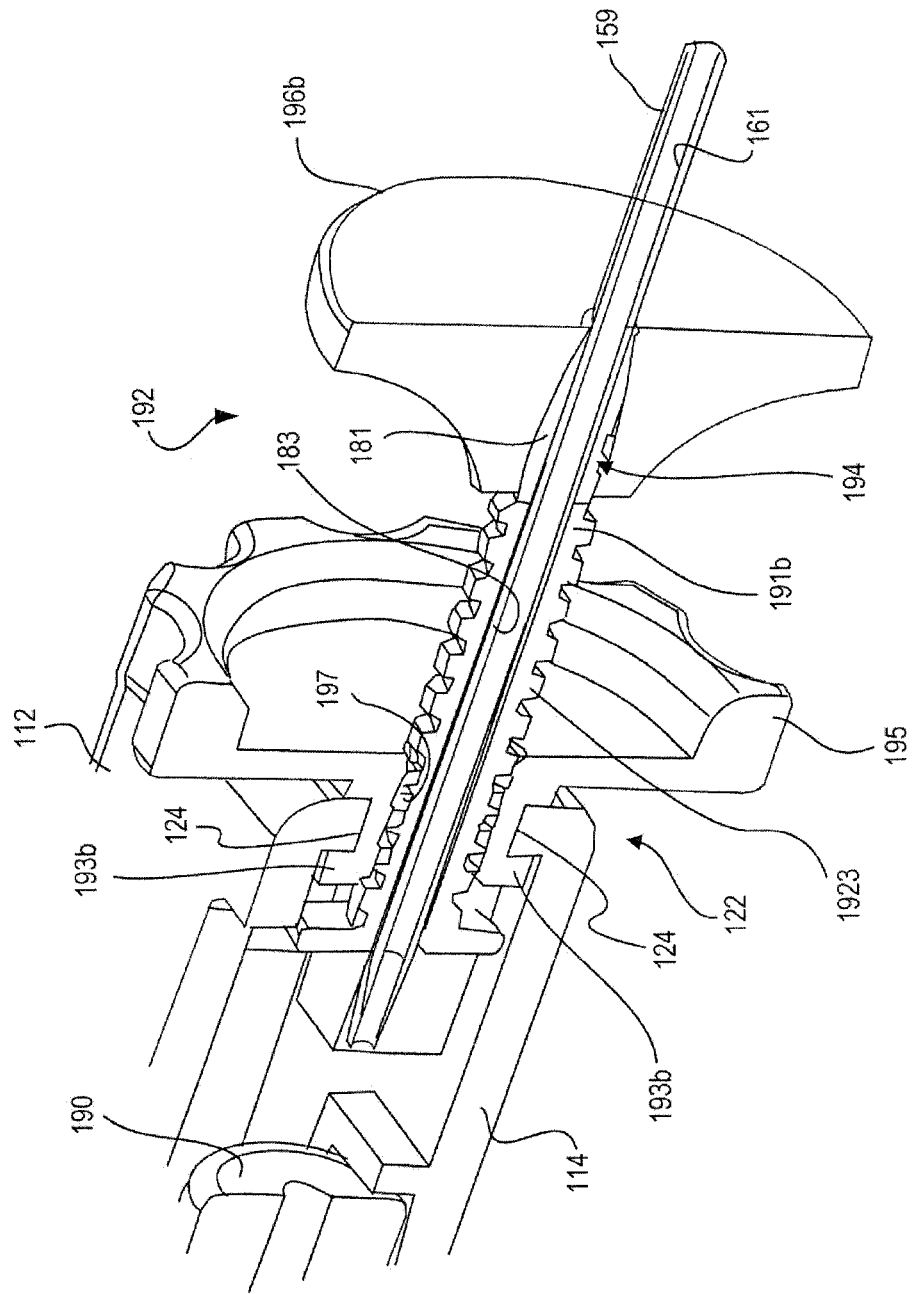
FIG. 8D is a side-perspective, cross-sectional view of the proximal end of the handle portion of a steerable introducer sheath assembly in accordance with an embodiment of the present disclosure.

Steerable introducer sheath assemblies embodying the present disclosure comprise an introducer sheath portion that extends in a distal fashion from a handle portion that may be held and manipulated by a user. One or more steering cables are affixed to the distal end of the introducer sheath, passed proximally through longitudinal steering cable lumens within the introducer sheath to the interior of the handle portion, wherein the proximal ends of the steering cables are engaged by at least one mechanism that allows a user to manipulate the distal end of the introducer sheath by selectively increasing or decreasing the steering cable tension. The precise location at which the distal ends of the steering cables are affixed at or near the distal tip of the introducer sheath may be varied proximally or distally, as necessary, to provide for the desired amount of distal curvature modification when the steering cable tension is increased or decreased. The introducer sheath portion further contains a longitudinal device lumen that is capable of slidably receiving a catheterized instrument, which can include a dilator (as depicted in FIGS. 8C and 8D, for example) through which standard length Bayliss RF transseptal devices (available from Bayliss Medical, Montreal, Canada), Brockenbrough transseptal needles, or other similar instruments. The handle portion further contains features that allow the user to finely control the advancement of the catheterized instrument through the introducer sheath.

Figure 3A:
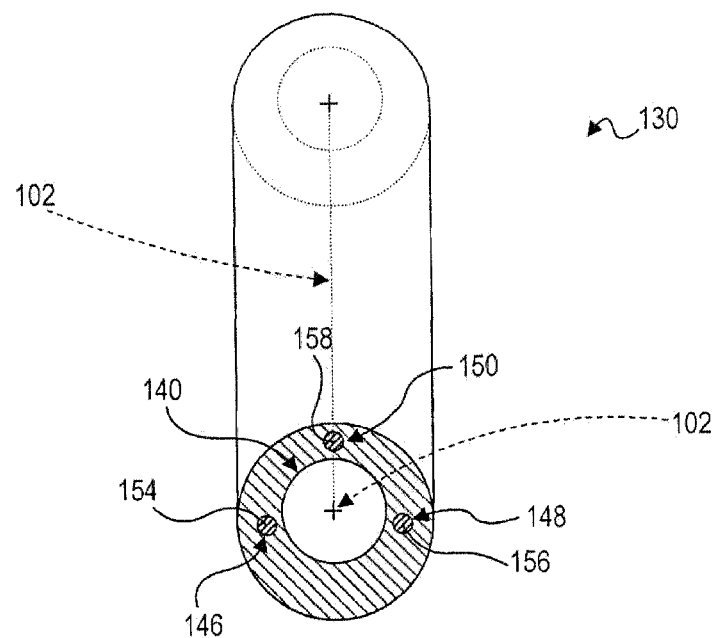
FIG. 3A provides cross-sectional views of a "four lumen" introducer sheath for use with a steerable introducer sheath assembly in accordance with an embodiment of the present disclosure.
Figure 3A:
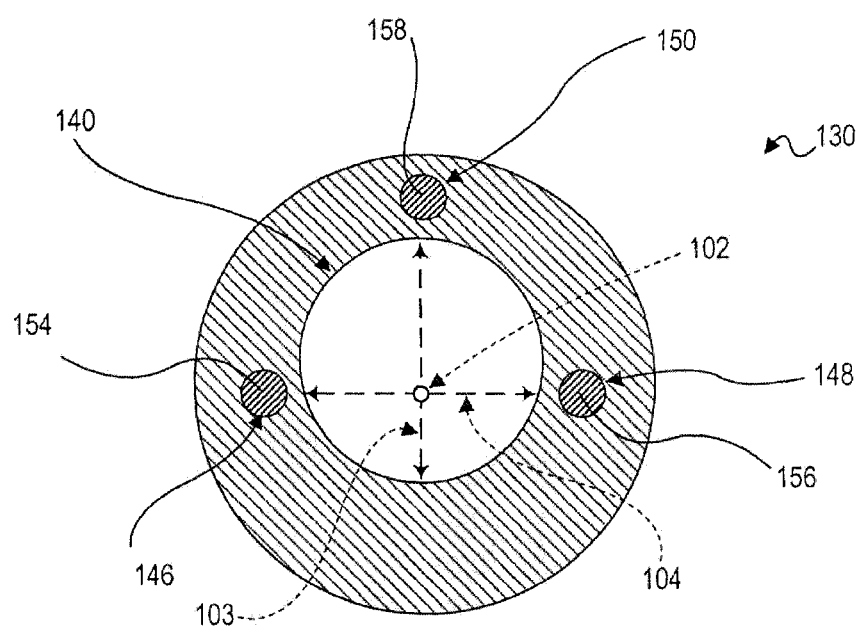

FIGS. 1A and 3A illustrate exemplary features of a steerable introducer sheath assembly in accordance with an embodiment of the present disclosure. As best shown in FIG. 1A, the steerable introducer sheath assembly may include a handle portion 110, and an introducer sheath 130 extending outwardly from the distal end (116) of handle portion 110. As best shown in FIG. 3A (depicting a planar cross section of introducer sheath 130 that is perpendicular to longitudinal center axis 102), introducer sheath 130 may contain a more or less centrally located device lumen 140 that is configured to slidably receive a catheterized instrument (e.g., dilator 159 shown in FIGS. 8A and 8C, and discussed herein), first and second steering cable lumens 146 and 148 in which are slidably disposed first and second steering cables 154 and 156 (respectively), and third steering cable lumen 150, in which is slidably disposed third steering cable 158.

Figure 1B:
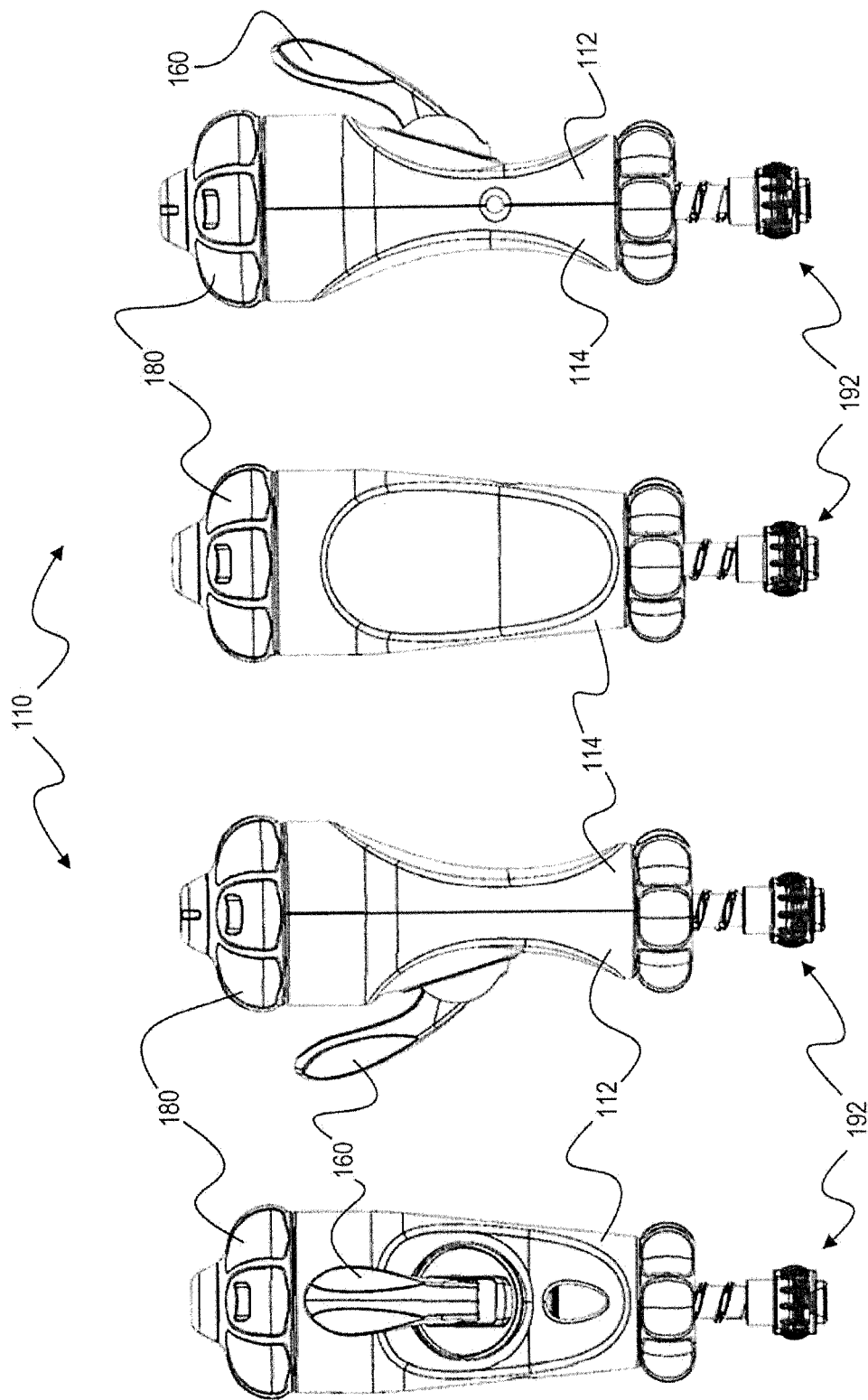
FIG. 1B provides top, bottom, and side views of the handle portion of a steerable introducer sheath assembly in accordance with an embodiment of the present disclosure.
Figure 1C:
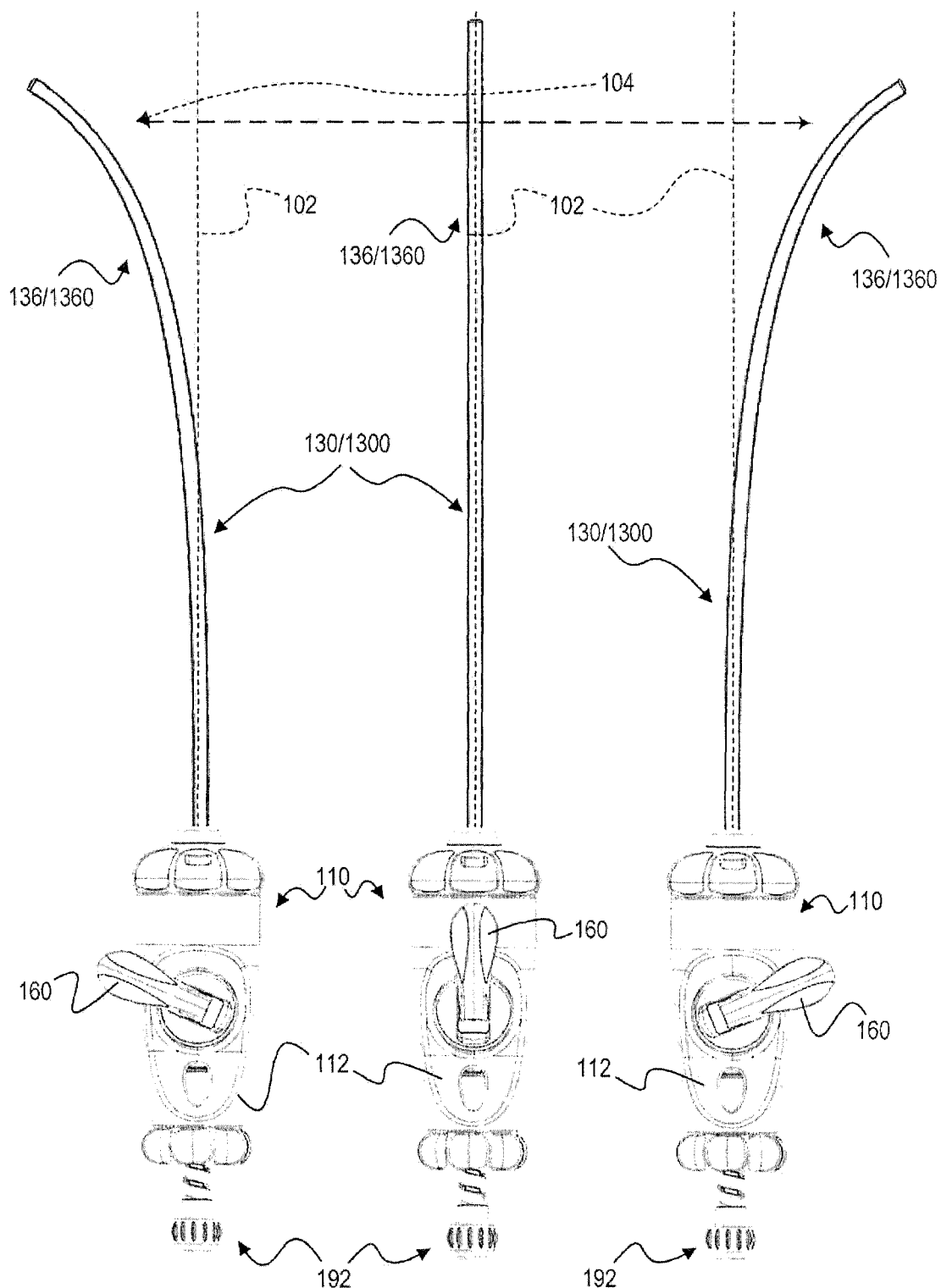
FIG. 1C provides top views of a steerable introducer sheath assembly in accordance with an embodiment of the present disclosure.
Figure 1D:
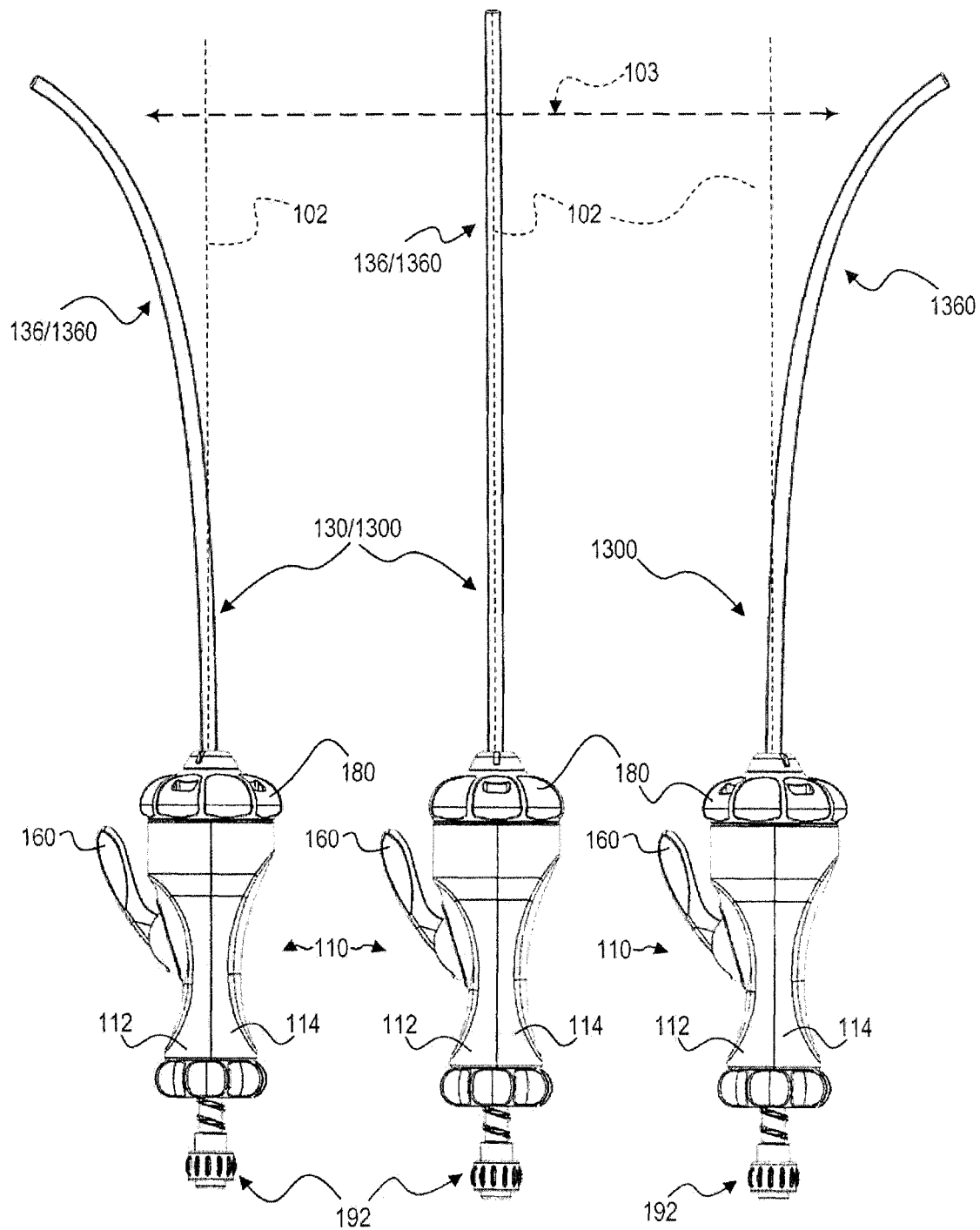
FIG. 1D provides side views of a steerable introducer sheath assembly in accordance with an embodiment of the present disclosure.

Referring again to the introducer sheath depicted in FIG. 3A, first and second steering cable lumens 146 and 148 may be disposed on opposite sides of device lumen 140, along a horizontal plane formed by horizontal axis 104 and longitudinal center axis 102, and symmetric about a vertical plane formed by vertical axis 103 and longitudinal center axis 102, with the horizontal and vertical planes being perpendicular to each other. As such, adjusting the tension in first and second steering cables 154 and 156 adjusts the "horizontal" curvature of the introducer sheath's distal portion 132 to the left or right of the vertical plane, while minimizing the potential unintended motion within the vertical plane. As further depicted in FIG. 3A, third steering cable lumen 150 and device lumen are disposed along the vertical plane, with third steering cable lumen 150 disposed above device lumen 140 (i.e. closer to a user viewing the steerable introducer sheath from the "top" view illustrated in FIG. 1C). As such, adjusting tension on third steering cable 158 will adjust the "vertical" curvature of distal portion 132 of introducer sheath 130 within the vertical plane while minimizing any unwanted deflection of introducer sheath 130 to the left or right of the vertical plane. In other words, when an operator views sheath assembly 100 from the proximal handle portion 110 and looks distally along introducer sheath 130 as it extends outwardly in an undeflected position, first steering cable 154 and second steering cable 156 may be utilized to effect "horizontal" curvature of the distal portion 132 of introducer sheath 130 to the left and to the right, respectively, of axis 102 (as best shown in FIG. 1C), and third steering cable 158 may be utilized to adjust the amount of "vertical" curvature of distal portion 132 of the introducer sheath 130, thereby lifting distal portion 132 "upwards" (i.e. towards the user) from axis 102 (as best shown in FIG. 1D).

Figure 3B:
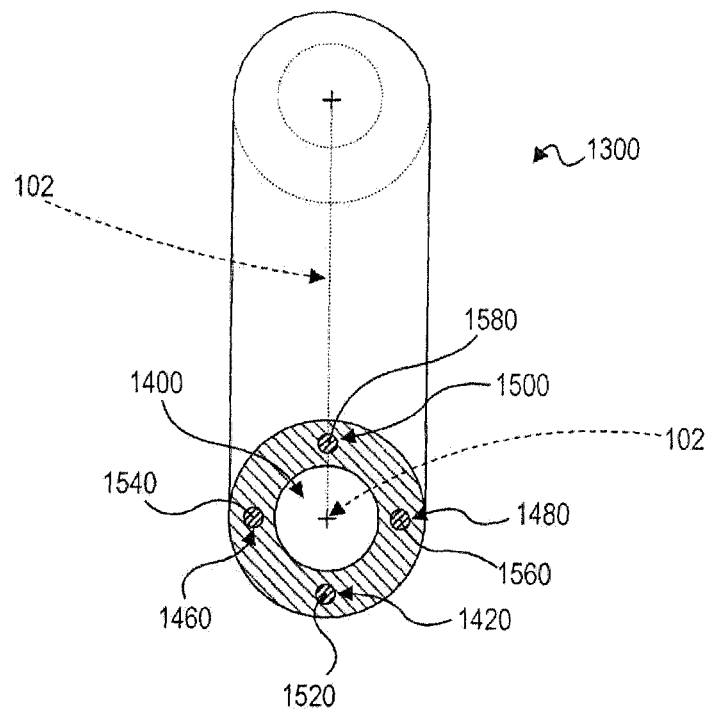
FIG. 3B provides cross-sectional views of a "five lumen" introducer sheath for use with a steerable introducer sheath assembly in accordance with an embodiment of the present disclosure.
Figure 3B:
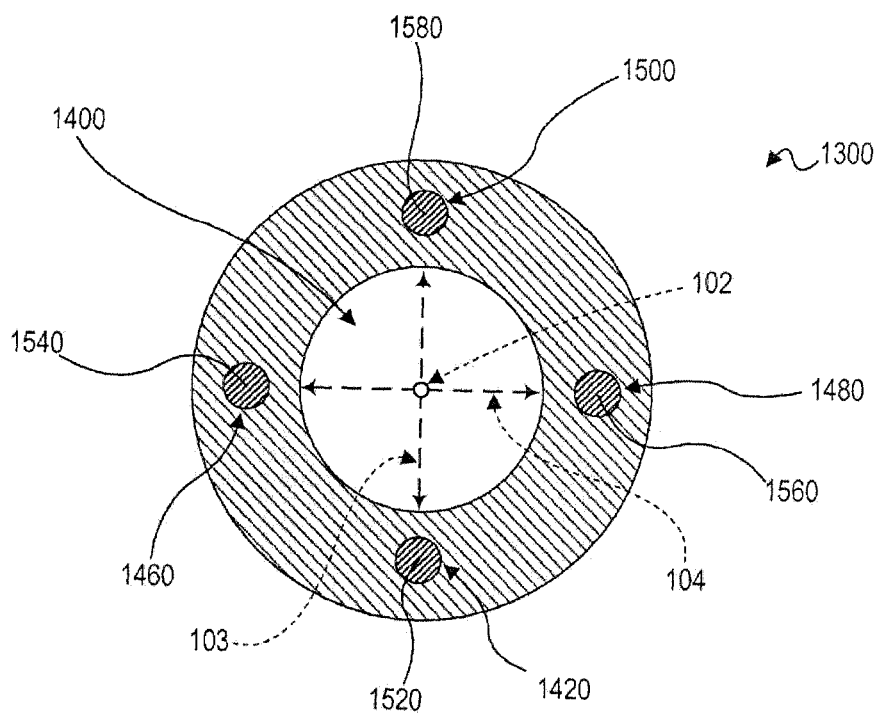

Other embodiments of the steerable introducer sheath assembly of the present disclosure may include an introducer sheath as depicted in FIG. 3B (depicting a planar cross section of introducer sheath 1300 that is perpendicular to longitudinal center axis 102), which contains a more or less centrally located device lumen 1400 that is configured to slidably receive a catheterized instrument (e.g., dilator 159 shown in FIGS. 8A and 8C, and discussed herein), first and second steering cable lumens 1460 and 1480 in which are slidably disposed first and second steering cables 1540 and 1560 (respectively), and third and fourth steering cable lumens 1500 and 1420, in which are slidably disposed third and fourth steering cables 1580 and 1520 (respectively). As further depicted in FIG. 3B, first and second steering cable lumens 1460 and 1480 are disposed on opposite sides of device lumen 1400, along a horizontal plane formed by horizontal axis 104 and longitudinal center axis 102, and symmetric about a vertical plane formed by vertical axis 103 and longitudinal center axis 102, with the horizontal and vertical planes being perpendicular to each other. Third and fourth steering cable lumens 1500 and 1420 are disposed on opposite sides of device lumen 140, along the vertical plane formed by vertical axis 103 and longitudinal center axis 102, and symmetric about the horizontal plane formed by horizontal axis 104 and longitudinal center axis 102.

For introducer sheaths with the cable arrangement shown in FIG. 3B, adjusting the tension in first and second steering cables 1540 and 1560 modifies the "horizontal" curvature of the distal portion of the introducer sheath in the direction of horizontal axis 104 (i.e., to the left or right of the vertical plane). This is best shown in FIG. 6C, which depicts introducer sheath 1300 with "horizontal" curvature to the left of the vertical plane (FIG. 6C, left), introducer sheath 1300 with no "horizontal" curvature (FIG. 6C, center), and introducer sheath 1300 with "horizontal" curvature to the right of the vertical plane (FIG. 6C, right). Similarly, adjusting the tension in third and fourth steering cables 1580 and 1520 modifies the "vertical" curvature of the distal portion of the introducer sheath in the direction of vertical axis 103 (i.e., curving either above or below the horizontal plane). This is best shown in FIG. 6D, which depicts introducer sheath 1300 with "vertical" curvature below the horizontal plane (FIG. 6D, left), introducer sheath 1300 with no "vertical" curvature (FIG. 6D, center), and introducer sheath 1300 with "vertical" curvature above the horizontal plane (FIG. 6D, right).

The handle portion of a steerable introducer sheath assembly in accordance with an embodiment of the present disclosure includes features that allow a user to selectively increase or decrease the steering cable tension in order to achieve a desired "horizontal" or "vertical" curvature to the distal portion of the introducer sheath. As best illustrated in FIGS. 1B-1D, for example, handle portion 110 may include a steering lever 160 for adjusting the tension in the first and second steering cables so as to modify the "horizontal" curvature of distal portion 132 of introducer sheath 130 (as best depicted in FIG. 1C and further discussed below), and a distal end cap 180 for adjusting the tension in the third steering cable so as to modify the "vertical" curvature of distal portion 132 of introducer sheath 130 (as best depicted in FIG. 1D and further discussed below).

Figure 2A:
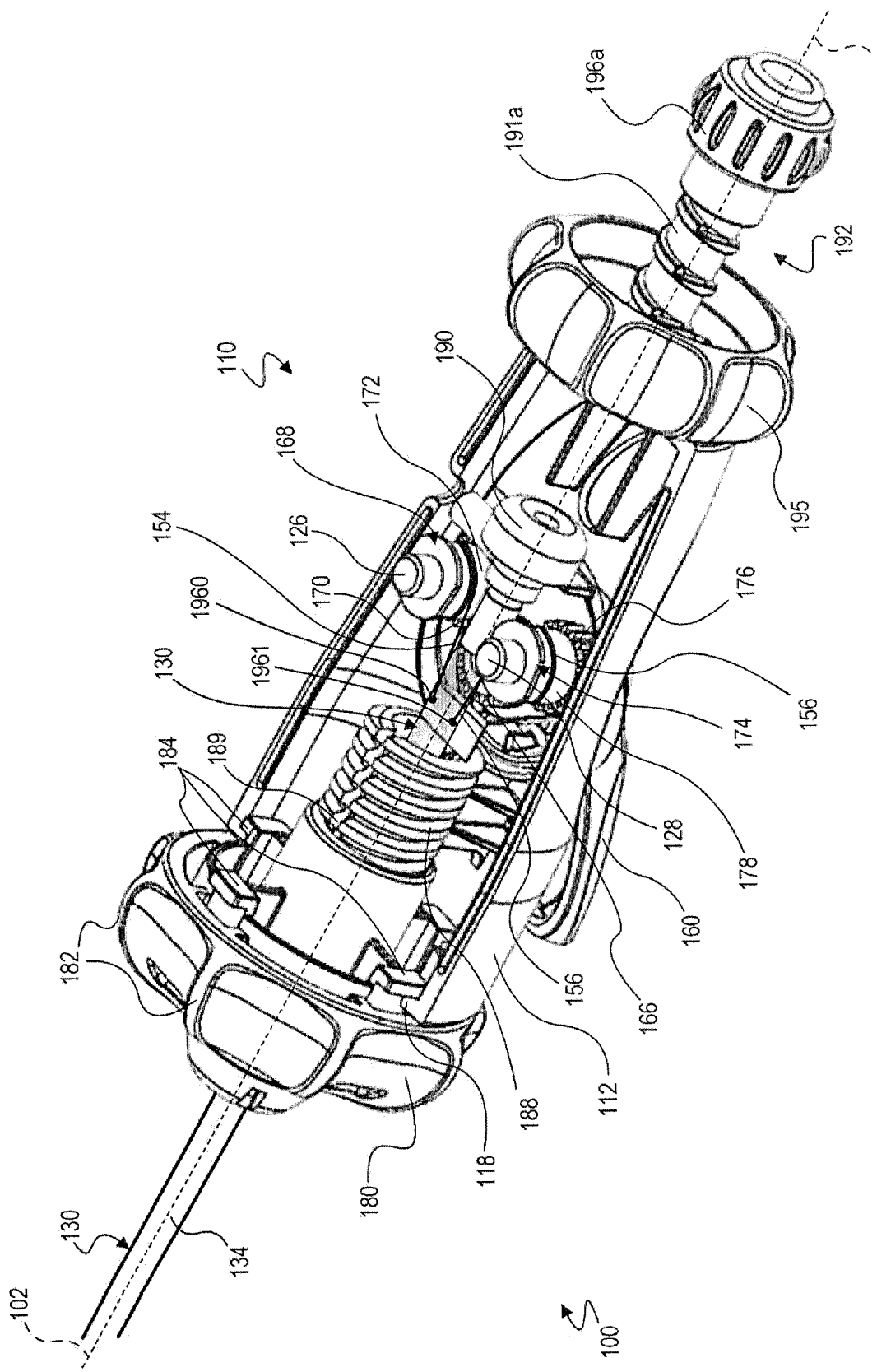
FIG. 2A is a partial, bottom view of the handle portion of a steerable introducer sheath assembly in accordance with an embodiment of the present disclosure, with the bottom portion of the handle housing removed to permit visualization of interior elements.
Figure 5A:
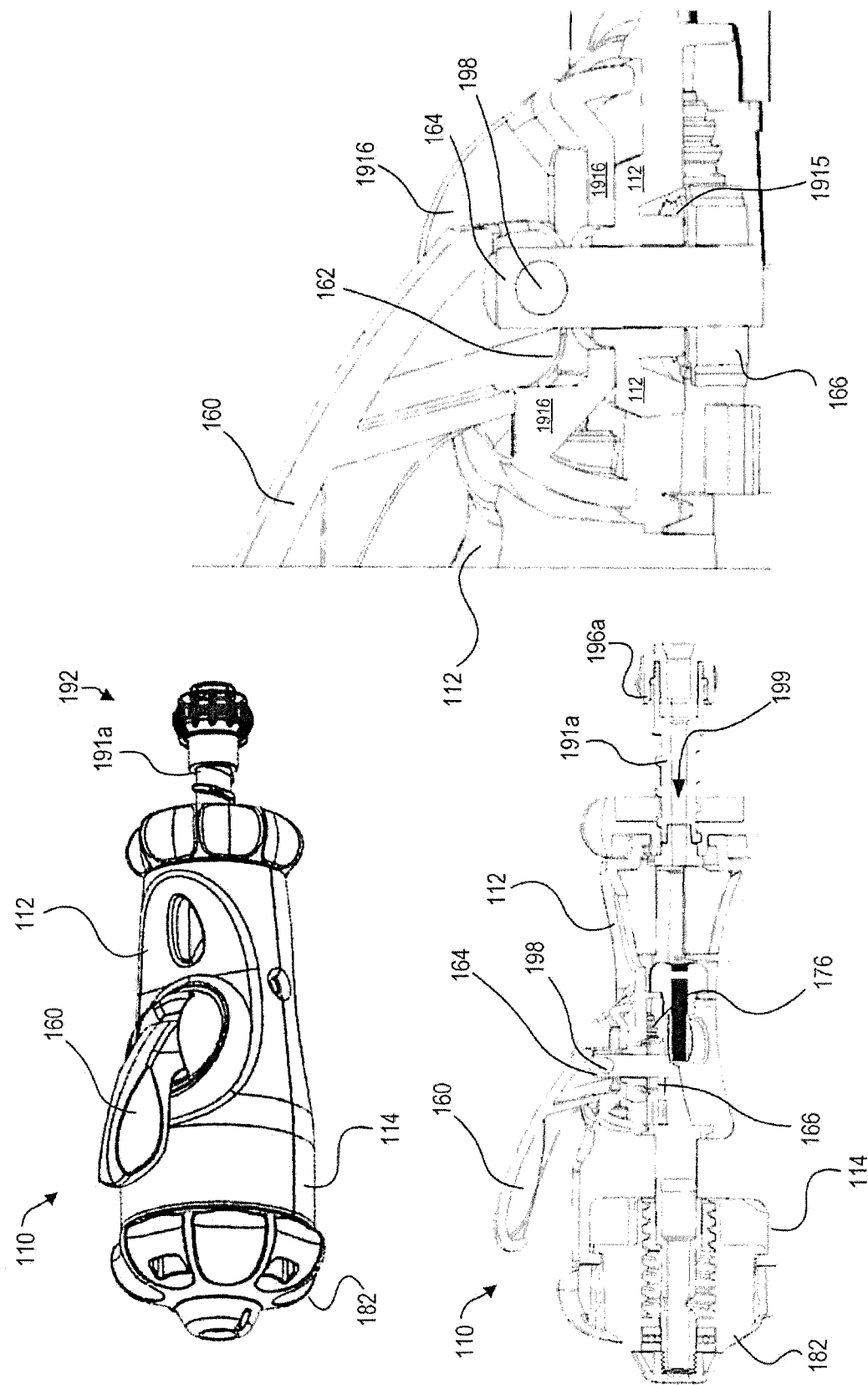
FIG. 5A provides perspective and cross-sectional views of the handle portion of a steerable introducer sheath assembly in accordance with an embodiment of the present disclosure, with an inset to show additional cross-sectional detail, and depicting steering lever 160 in an "unlocked" position.
Figure 5B:
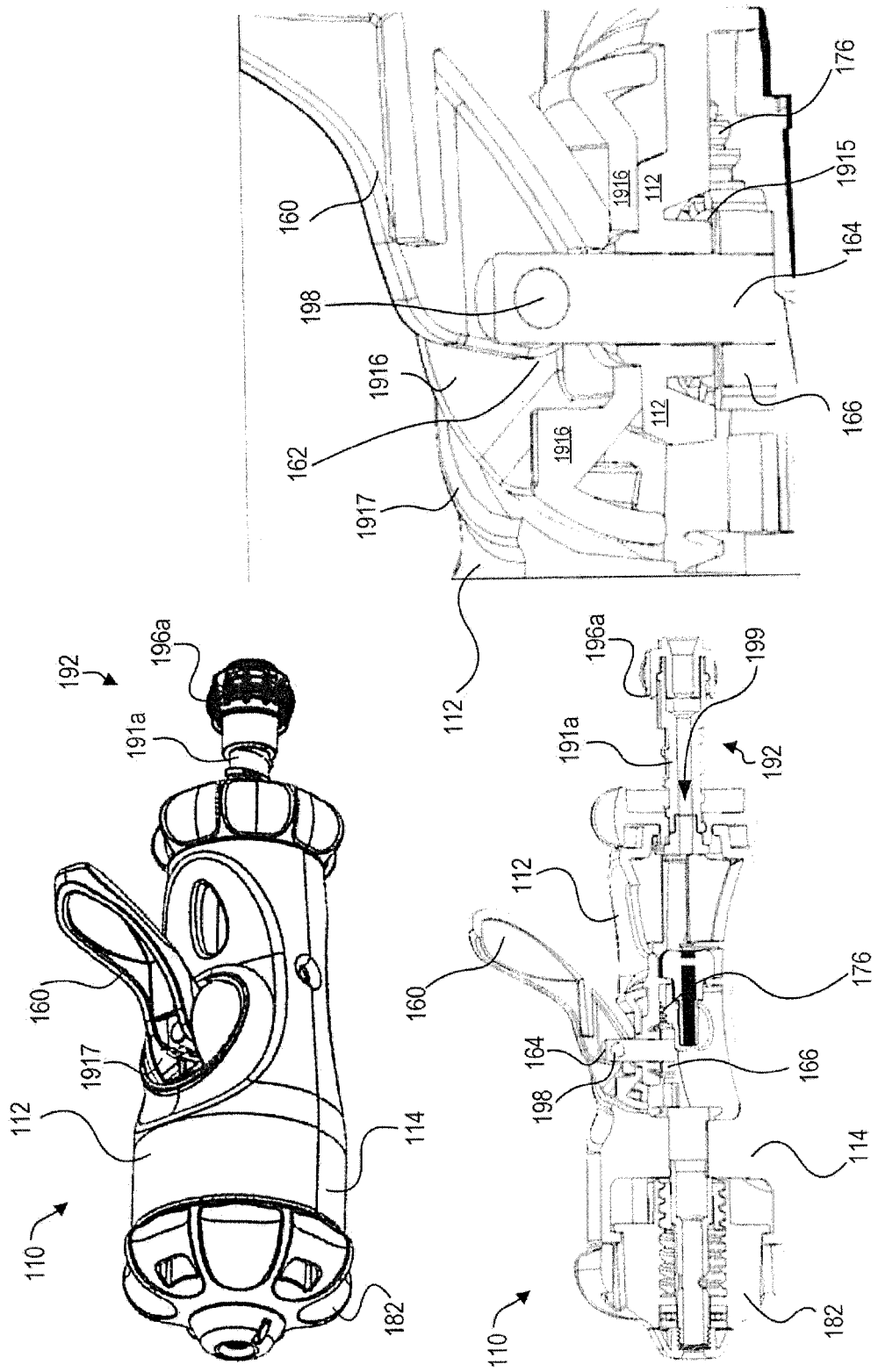
FIG. 5B provides perspective and cross-sectional views of the handle portion of a steerable introducer sheath assembly in accordance with an embodiment of the present disclosure, with an inset to show additional cross-sectional detail, and depicting steering lever 160 in a "locked" position.
Figure 5C:
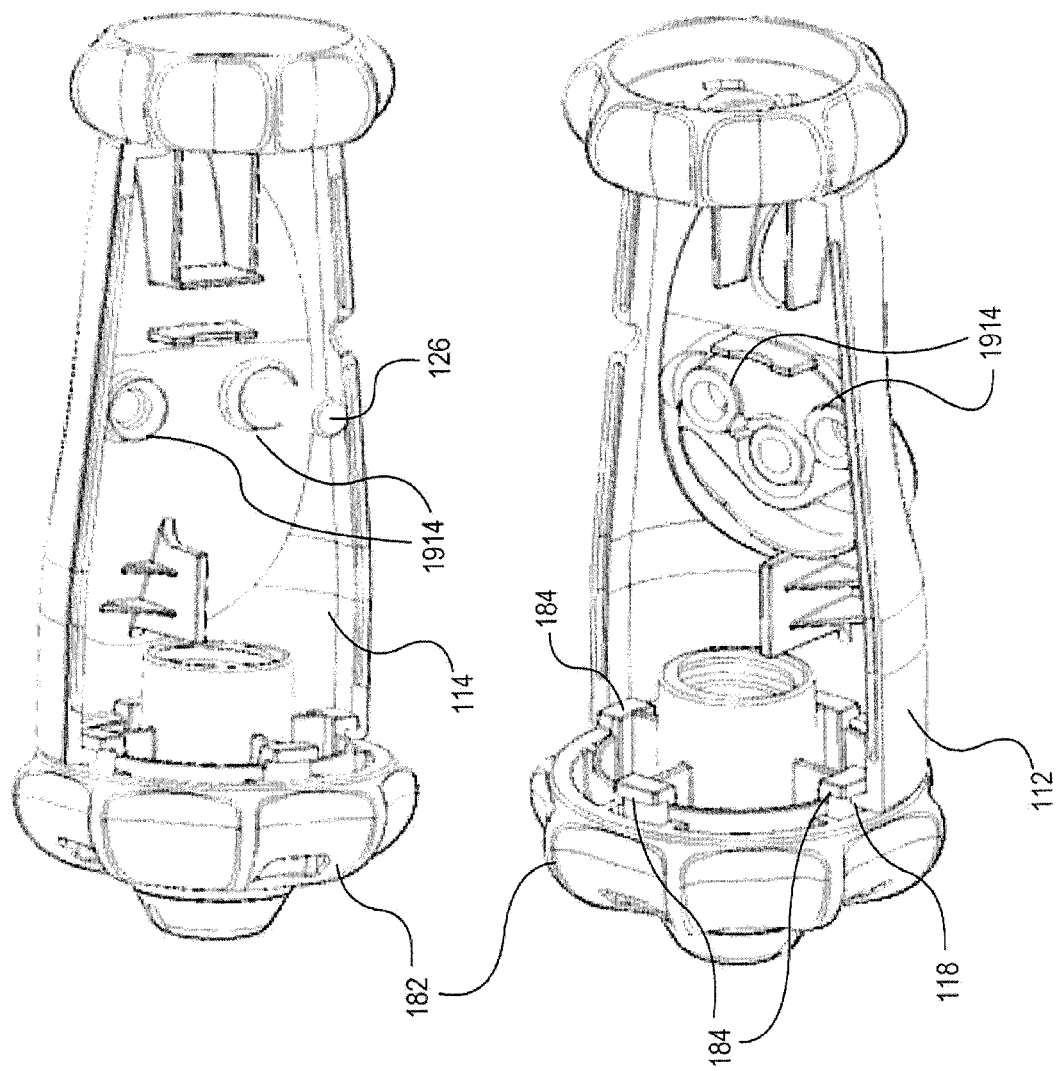
FIG. 5C provides cut-away views of the interior faces of the upper and lower portions of a handle of a steerable introducer sheath assembly in accordance with an embodiment of the present disclosure.

In certain embodiments the mechanism for manipulating first steering cable 154 and second steering cable 156 to adjust the amount of "horizontal" curvature of distal portion 132 of the introducer sheath may comprise an external steering lever 160 that controls an internal system of drive gears and rotational posts that are coupled to steering cables 154 and 156. As best illustrated in FIGS. 2A, 5A, and 5B, for example, a steering lever 160 may be pivotably secured to a first end of a steering post 164 by way of bores that align to receive steering lever pin 198. Steering post 164 is non-rotatably secured to a drive gear 166 at its second end. Drive gear 166 is situated within handle 100 so that is capable of simultaneously engaging and rotating both a first gear assembly 168, and a second gear assembly 174. As best shown in FIG. 2A, first and second gear assemblies 168 and 174 may each comprise a rotatable post (126, 128) that extends inwardly from a housing on the interior of handle 100, a non-rotatably-secured barrel portion (172, 178), and a non-rotatably-secured gear (170, 176) that engages drive gear 166. Posts 126 and 128 may be situated perpendicular to center axis 102 (as depicted in FIGS. 2A, 5A, and 5B, for example), or alternatively at a non-perpendicular angle to center axis 102. Posts 126 and 128 may be rotationally engaged by retaining features extending inwardly from the interior faces of the upper housing portion 112, the lower housing portion 114, or both. For example, as best shown in FIG. 5C (depicting seating flanges and showing the engagement of post 126 with a seating flange 1914 in lower housing portion 114), in some embodiments posts 126 and 128 may be rotationally engaged by circular seating flanges 1914 in upper housing portion 112 and lower housing portion 114.

As briefly noted above and best illustrated in FIGS. 1A and 2A, the distal ends of first steering cable 154 and second steering cable 156 are affixed at or near the distal tip 136 of introducer sheath, with the cables themselves extending proximally through steering lumens 146 and 148 (respectively) until the proximal ends terminate in the interior of handle portion 110, wherein the proximal ends of both cables may be engaged by one or more steering mechanisms that are capable of selectively increasing or decreasing the tension in the steering cables.

For example, as best shown in FIG. 2A, first and second steering cables 154 and 156 may exit introducer sheath 130 via respective openings 1960 and 1961, which are located near the terminal portion of introducer sheath 130 (i.e., the portion that is located inside of handle portion 110). In this way, the proximal ends of first and second steering cables 154 and 156 are able to pass out of steering lumens 146 and 148 (respectively), and become engaged with first and second steering gear assemblies 168 and 174 (respectively). For embodiments of the steerable introducer sheath assembly of the present disclosure that include an introducer sheath similar to introducer sheath 1300 that is shown in FIG. 3B, the proximal ends of first and second steering cables 1540 and 1560 pass out of first and second steering cable lumens 1460 and 1480 (respectively) via similar openings to those shown in FIG. 2A (1960 and 1961), and become engaged with first and second steering gear assemblies 168 and 174 (respectively).

As best shown in FIG. 2A, for example, in some embodiments the proximal end of first steering cable 154 is affixed to barrel portion 172 of first gear assembly 168, and the proximal end of second steering cable 156 is affixed to barrel portion 178 of second gear assembly 174. Drive gear 166 is engaged with both first gear 170 and second gear 176 such that rotation of drive gear 166 causes first and second gear assemblies 168 and 174 to rotate simultaneously, thereby adjusting the tension applied to first and second steering cables 154 and 156, which are affixed to and wrapped around barrel portions 172 and 178, respectively, in a manner such that when the tension in one of the steering cables is increased due to rotation of steering lever 160, the tension in the other steering cable is decreased. As such, first and second steering cables 154 and 156 work in unison to either increase or decrease the "horizontal" curvature of distal portion 132 to either the left or right of axis 102.

In certain embodiments, first and second steering cables 154 and 156 are affixed to and engaged by barrel portions 172 and 178, respectively in such a manner that, viewing handle portion 110 from the "top" as best illustrated in FIG. 1C, turning steering lever 160 in a counterclockwise fashion (i.e. so that the distal end of steering lever 160 points more to the "left" with respect to longitudinal center axis 102) causes the distal portion (136) of introducer sheath 130 to become "horizontally" curved more to the left of longitudinal center axis 102 (FIG. 1C, at left), turning steering lever 160 in a clockwise fashion (i.e. so that the distal end of steering lever 160 points more to the "right" with respect to longitudinal center axis 102) causes the distal portion (136) of introducer sheath 130 to become "horizontally" curved more to the right of longitudinal center axis 102 (FIG. 1C, at right), and returning steering lever 160 to the center position (i.e. so that the distal end of steering lever 160 points in a parallel direction to longitudinal center axis 102) causes distal portion (136) of introducer sheath 130 to extend in a parallel direction to longitudinal center axis 102 (i.e. with no "horizontal" curvature, as in FIG. 1C, at center). In this fashion, the orientation of the distal end of steering lever 160 may provide the user with an indication as to the presence, directionality, and relative extent of any "horizontal" curvature that has been introduced to the distal portion (136) of introducer sheath 130.

In alternative embodiments, first and second steering cables 154 and 156 may be affixed to and engaged by barrel portions 172 and 178 such that turning the steering lever in a "counterclockwise" fashion will cause the distal portion (136) of introducer sheath 130 to be "horizontally" curved to the right, and vice-versa.

In certain embodiments of the steerable introducer sheath assembly in accordance with the present disclosure, the interactions between steering lever 160, drive gear 166 and/or first and second gear assemblies 168 and 174 may be modified to either increase or decrease the "sensitivity" of steering lever 160 (i.e. the extent to which "horizontal" curvature is introduced when steering lever 160 is rotated to a particular degree). For example, in certain embodiments a variable transmission may be provided that allows the user to modulate the "sensitivity" of steering lever 160 by selectively modifying the gearing ratios between drive gear 166 and/or first and second gear assemblies 168 and 174. Alternatively, spring-loaded gear posts and/or flywheel assemblies may be provided for modulating the sensitivity of steering lever 160 in a desired fashion.

In certain embodiments, the steerable introducer sheath assembly may include a mechanism for locking the steering lever in place once a desired amount of curvature has been achieved for the introducer sheath. As shown in FIGS. 5A and 5B, for example, steering lever 160 may include a camming surface 162, such that when steering lever 160 is rotated upwardly about steering lever pin 198 from the "unlocked" position (FIG. 5A) to the "locked" position (FIG. 5B), camming surface 162 becomes frictionally engaged with the outer surface of upper handle portion 112, and steering post 164 is lifted in a radial direction away from the interior of the handle such that drive gear 166 becomes frictionally engaged with the interior surface of upper handle portion 112. In certain embodiments, this "locking" friction may be modulated by providing one or more washers to separate drive gear 166 and the interior surface of upper handle portion 112, which may for example include wave spring washer 1915 depicted in FIGS. 5A and 5B.

Figure 5D:
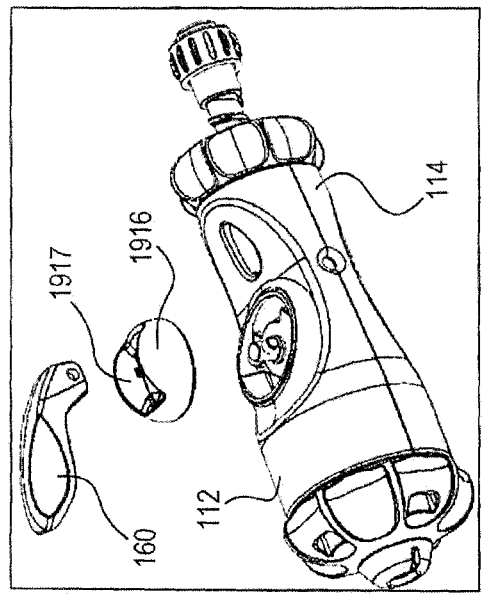
FIG. 5D provides top and perspective views of a handle of a steerable introducer sheath assembly in accordance with an embodiment of the present disclosure, with the steering lever and associated dome cover separated and/or rotated with respect to the handle.
Figure 5D:
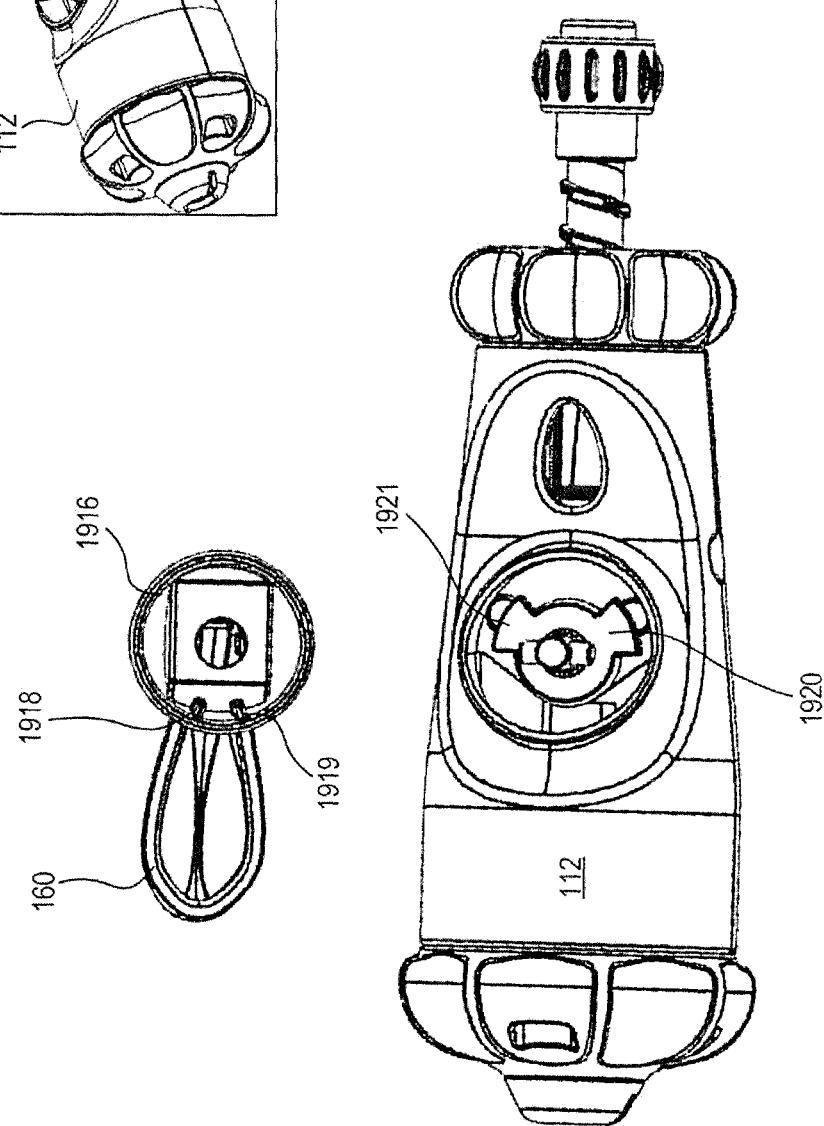

As shown in FIGS. 5A, 5B, and 5D, certain embodiments may include a dome cover 1916 that sits within a dome cover recess 1917 extruding from the exterior face of upper handle portion 112, thereby mediating the interaction between camming surface 162 of steering lever 160, and the outer surface of upper handle portion 112. As best shown in FIG. 5D (inset), dome cover 1916 may be shaped to provide a central slot 1917 through which steering lever 160 protrudes, with recess 1917 of sufficient width to accommodate vertical rotation between the "unlocked" and "locked" positions, while also providing lateral support for steering lever 160 when it is manipulated to turn steering post 164, and further ensuring that when pivoted from the "unlocked" position (FIG. 5A) to the "locked" position (FIG. 5B), steering lever 160 is constrained to a direction that is perpendicular to the line of axis of steering lever pin 198.

In certain embodiments, dome cover 1916 and dome cover recess 1917 may be configured to limit the angular displacement of steering post 164 about its longitudinal axis when steering lever 160 is manipulated. As shown in FIG. 5D, for example, this may be achieved through flanges (1918 and 1919) that extend from the underside of dome cover 1916, and interact with the distal faces formed by corresponding protrusions 1920 and 1921 (respectively) to constrain the rotation of steering lever 160. This protects cables 154 and 156 from the excessive strain that could result from a user's attempt to overtighten them using steering lever 160. In certain embodiments, protrusions 1920 and 1921 and/or flanges 1918 and 1919 may be adjustable, so that the extent to which the rotation of steering lever 160 is restricted can be modified according to the user's preferences.

For embodiments of the steerable introducer sheath assembly of the present disclosure that feature introducer sheaths with the cable arrangement shown in FIG. 3B, a steering lever with the steering assembly mechanisms and other associated features described above may likewise be used to adjust the tension in first and second steering cables 1540 and 1560 to modify the "horizontal" curvature of the distal portion of the introducer sheath in the direction of horizontal axis 104 (i.e., to the left or right of the vertical plane). For such embodiments, first and second steering cables 1540 and 1560 are affixed to and engaged by barrel portions 172 and 178 in the same manner as described above (and illustrated in FIG. 2A) for first and second steering cables 154 and 156 from introducer sheath 130. As such, when viewed from the "top" as illustrated in FIGS. 1C and 6C, turning steering lever 160 in a counterclockwise fashion (i.e. so that the distal end of steering lever 160 points more to the "left" with respect to longitudinal center axis 102) causes the distal portion (1360) of introducer sheath 1300 to become "horizontally" curved more to the left of longitudinal center axis 102 (FIG. 6C at left), turning steering lever 160 in a clockwise fashion (i.e. so that the distal end of steering lever 160 points more to the "right" with respect to longitudinal center axis 102) causes the distal portion (1360) of introducer sheath 1300 to become "horizontally" curved more to the right of longitudinal center axis 102 (FIG. 6C, at right), and returning steering lever 160 to the center position (i.e. so that the distal end of steering lever 160 points in a parallel direction to longitudinal center axis 102) causes distal portion (1360) of introducer sheath 1300 to extend in a parallel direction to longitudinal center axis 102 (i.e. with no "horizontal" curvature, as in FIG. 6C, at center). Here again, the orientation of the distal end of steering lever 160 signifies the presence, directionality, and relative extent of any "horizontal" curvature that has been introduced to the distal portion (1360) of introducer sheath 1300.

This is best shown in FIG. 6C, which depicts introducer sheath 1300 with "horizontal" curvature to the left of the vertical plane (FIG. 6C, left), introducer sheath 1300 with no "horizontal" curvature (FIG. 6C, center), and introducer sheath 1300 with "horizontal" curvature to the right of the vertical plane (FIG. 6C, right). Similarly, adjusting the tension in third and fourth steering cables 1580 and 1520 modifies the "vertical" curvature of the distal portion of the introducer sheath in the direction of vertical axis 103 (i.e., curving either above or below the horizontal plane). This is best shown in FIG. 6D, which depicts introducer sheath 1300 with "vertical" curvature below the horizontal plane (FIG. 6D, left), introducer sheath 1300 with no "vertical" curvature (FIG. 6D, center), and introducer sheath 1300 with "vertical" curvature above the horizontal plane (FIG. 6D, right).

As previously mentioned, the handle portion of a steerable introducer sheath in accordance with an embodiment of the present disclosure may also include features that allow a user to selectively increase or decrease the steering cable tension in order to achieve a desired "vertical" curvature to the distal portion of the introducer sheath. For example, handle portion 110 may include a distal end cap 180 that controls the axial motion of externally-threaded stem 188, thereby adjusting the tension in the third steering cable so as to modify the "vertical" curvature of distal portion 132 as shown in FIG. 1D (at left and center).

Figure 2B:
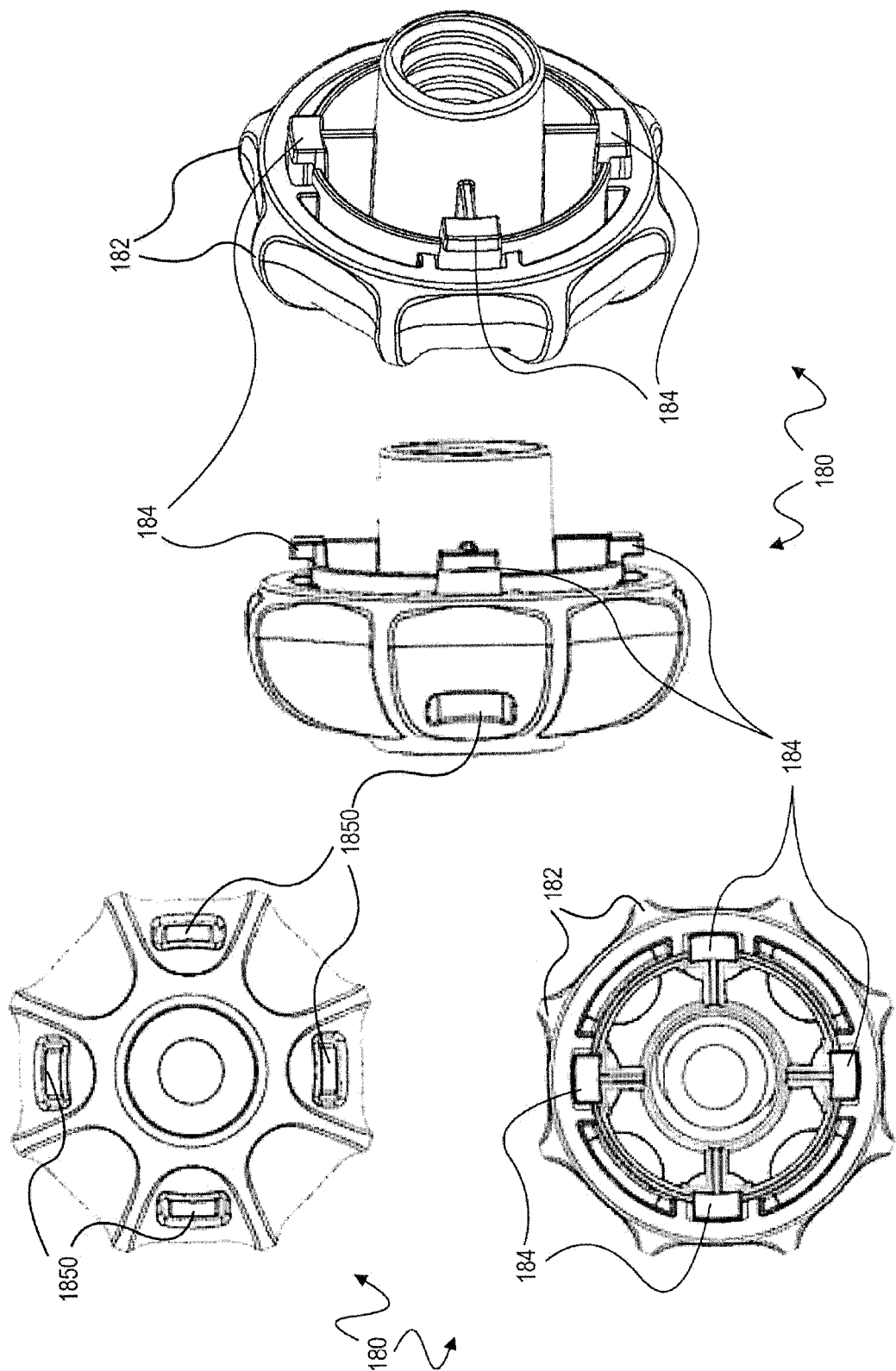
FIG. 2B provides distal, back, side, and perspective views of a distal end cap of a steerable introducer sheath assembly in accordance with an embodiment of the present disclosure.

As can be seen in FIGS. 1A-1D, handle portion 110 may include an upper housing portion 112 and a lower housing portion 114 that together define a distal aperture 118 disposed at the distal end (116) of handle portion 110. In certain embodiments, distal aperture 118 may be configured to rotatably receive distal end cap 180 so that distal end cap 180 is free to rotate relative to handle portion 110. For example, as illustrated in FIGS. 2A & 2B and 7B, distal end cap 180 may include a plurality of ridges 182 extending radially outwardly from the outer surface so that distal end cap 180 may be readily grasped and rotated during use. Distal end cap 180 may further include an internally threaded portion 186 that engages correspondingly threaded stem 188 that is disposed within handle portion 110. Distal end cap 180 may further include an outwardly depending radial flange that is disposed at its proximal end, the diameter of which is greater than the diameter of distal aperture 118, thereby allowing distal end cap 180 to be received and axially retained within annular cavity 120 that is defined by the joining of upper housing portion 112 and a lower housing portion 114 to form handle portion 110.

As best shown in FIGS. 2A-B and 7B, in certain embodiments the outwardly depending radial flange disposed at a proximal end of distal end cap 180 may be comprised of a plurality of tabs 184 with outwardly depending members that together define a discontinuous radial flange with a radius that is greater than that of distal aperture 118 so that distal end cap 180 may be received and axially retained within annular cavity 120. As best shown in FIG. 2B, distal end cap 180 may further include a plurality of vents 1850 corresponding to tabs 184 in an arrangement that facilitates the use of injection molding techniques to manufacture a distal end cap 180.

Figure 4A:
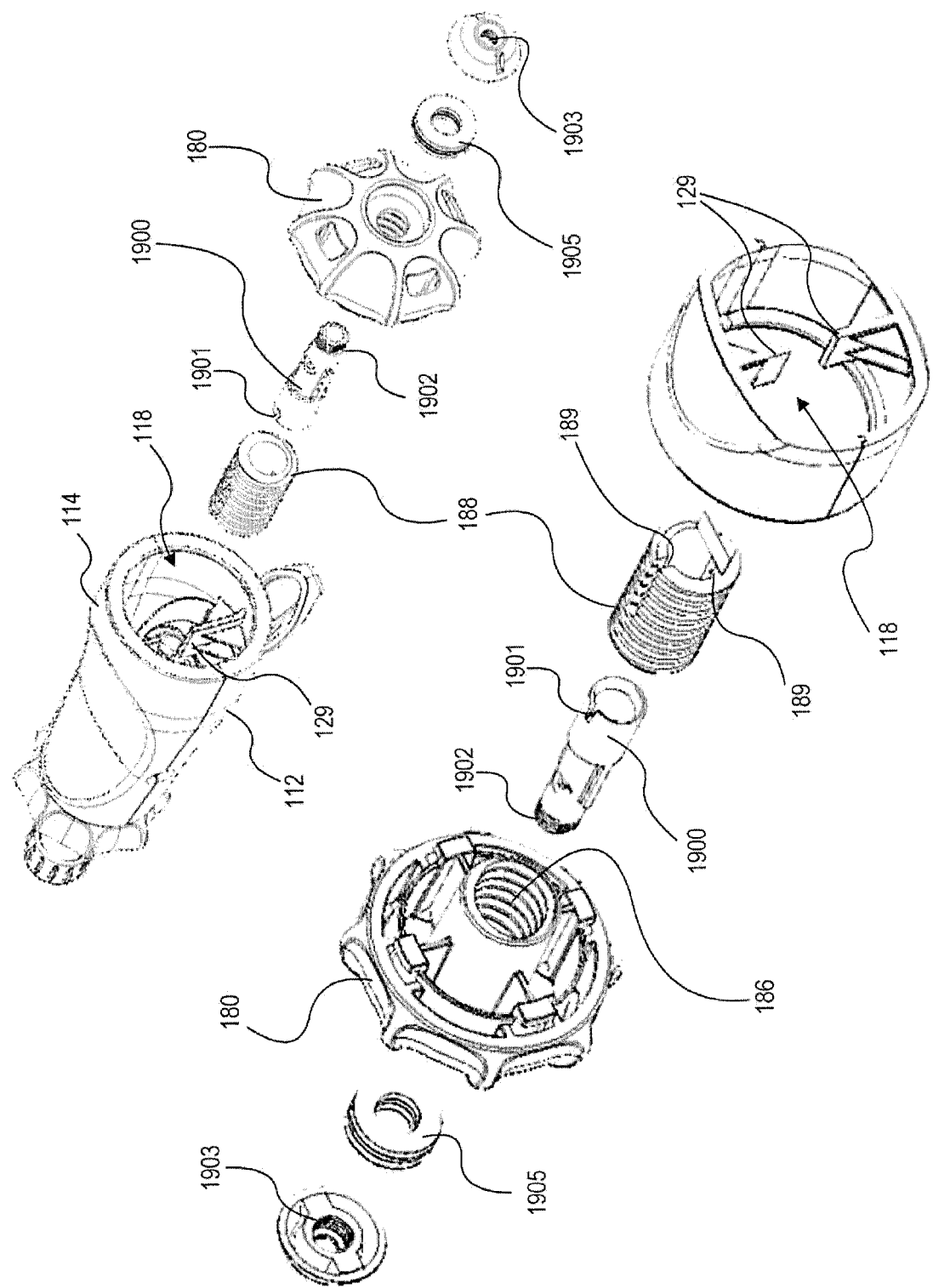
FIG. 4A provides exploded views of a torque transmission lock for use with a steerable introducer sheath assembly in accordance with an embodiment of the present disclosure.
Figure 4B:
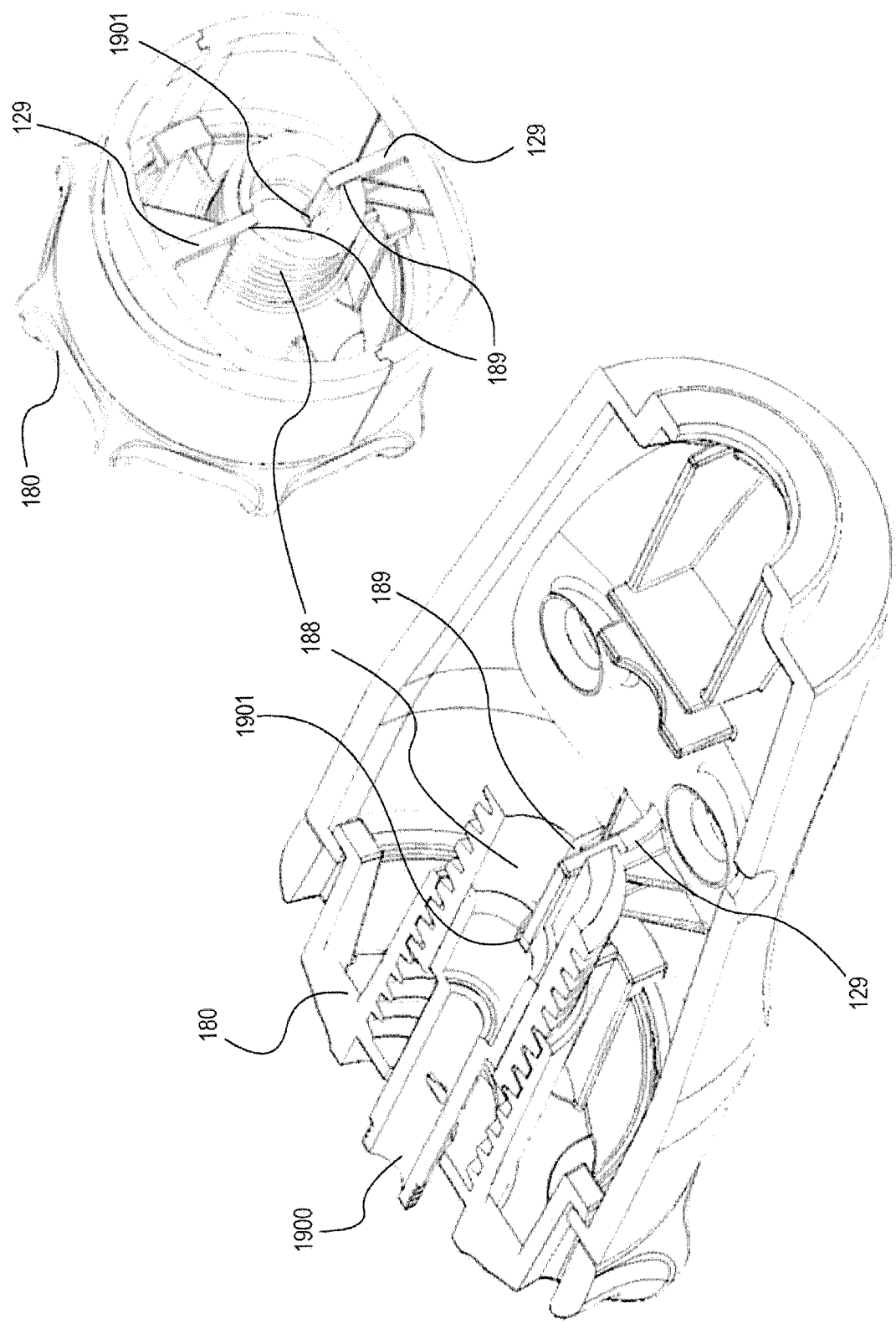
FIG. 4B provides cross-sectional views of a torque transmission lock for use with a steerable introducer sheath assembly in accordance with an embodiment of the present disclosure.

As can be seen in FIGS. 4A and 4B, externally-threaded stem 188 may include one or more axially extending slots 189 that can engage one or more axially extending flanges 129 that depend radially inwardly from an inner surface of handle 110. When distal end cap 180 is rotated, the engagement of slot(s) 189 and flange(s) 129 ensures that externally-threaded stem 188 does not also rotate, as a result of which externally-threaded stem 188 moves axially (i.e. parallel to longitudinal center axis 102) in either a proximal or distal direction when the user rotates distal end cap 180. As discussed in greater detail below, the axial motion of externally-threaded stem 188 that results from the rotation of distal end cap 180 is utilized to introduce "vertical" curvature to distal portion 132 of introducer sheath 130.

To ensure that force is properly transferred to the distal portion 132 of introducer sheath 130 during operation (for example, when the user increases or decreases the tension in one or more of the steering cables to introduce "horizontal" and/or "vertical" curvature to the proximal end of introducer sheath 130), the steerable introducer sheath in accordance with an embodiment of the present disclosure may further include a torque transmission lock that prevents introducer sheath 130 from rotating about longitudinal center axis 102. For example, as best shown in FIGS. 4A and 4B, certain embodiments may include a torque transmission lock 1900 comprising a hollow column with an external diameter that allows it to pass through the inner bore of externally-threaded stem 188, an internal diameter sufficient to encompass the radial diameter of introducer sheath 130, and a recess 1901 at its proximal end that is capable of engaging with flange 129. The distal end of torque transmission lock 1900 includes external threading 1902 that corresponds to the threading on the internal bore of transmission lock cap 1903. When threaded onto transmission lock 1900, the proximal face of transmission lock cap 1903 is capable of movably engaging with the distal face of distal end cap 180 to secure transmission lock 1900 within the bore of externally-threaded stem 188, with recess 1901 fully engaged to flange 129. In certain embodiments, the movable engagement between transmission lock cap 1903 and distal end cap 180 may be facilitated through the use of a thrust bearing 1905 that may be seated within an indentation 1904 on the distal face of distal end cap 180. In the final assembly, introducer sheath 130 is passed through the bore of torque transmission lock 1900 and immovably affixed thereto, and thus the engagement of recess 1901 with flange 129 prevents introducer sheath 130 from rotating about longitudinal center axis 102 when "vertical" curvature is introduced using distal end cap 180, or when "horizontal" curvature is introduced using steering lever 160.

Figure 2C:
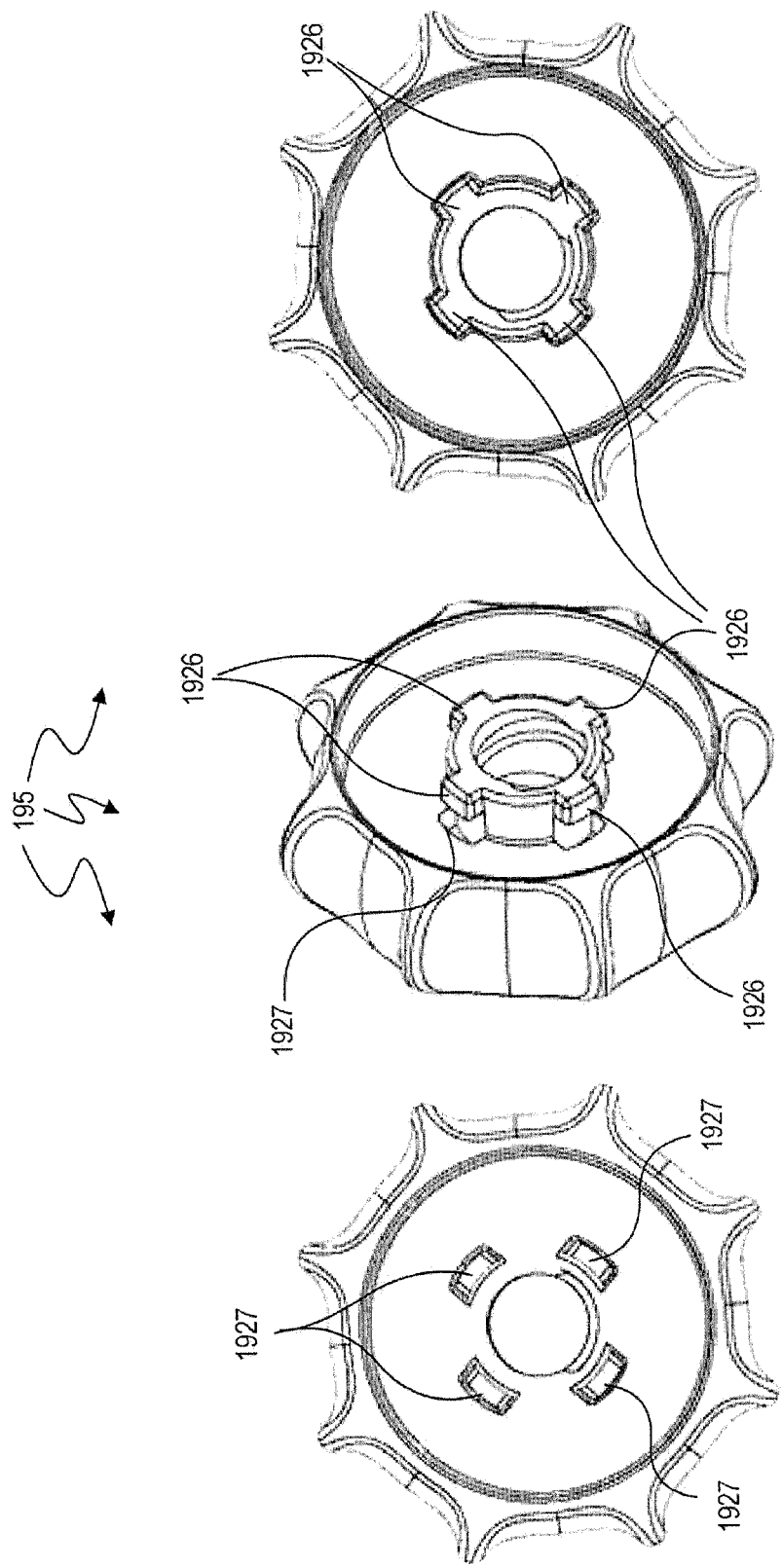
FIG. 2C provides distal, back, and perspective views of an advance knob of a steerable introducer sheath assembly in accordance with an embodiment of the present disclosure.
Figure 2D:
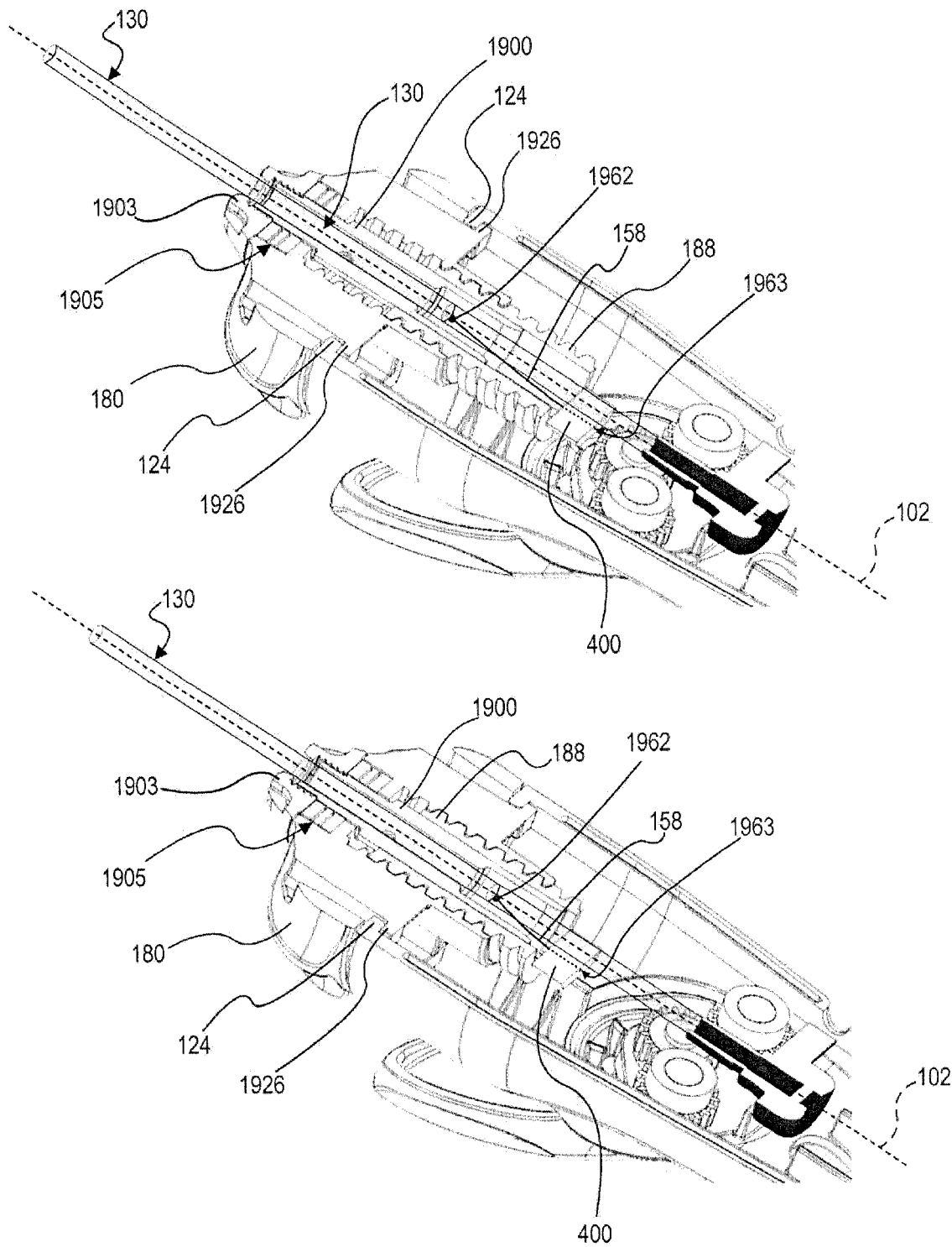
FIG. 2D is a partial, bottom view of the handle portion of a steerable introducer sheath assembly in accordance with an embodiment of the present disclosure, with the bottom portion of the handle housing removed to permit visualization of interior elements.

The proximal terminus of third steering cable 158 may be affixed to externally-threaded stem 188 such that the tension of third steering cable 158 may be increased or decreased by rotating distal end cap 180, which causes externally-threaded stem 188 to move distally or proximally along axis 102. As best shown in FIGS. 1A and 2D, for example, the distal terminus of third steering cable 158 is affixed at or near the distal tip 136 of introducer sheath 130, and from there extends proximally through steering lumen 150 until the proximal end terminates in the interior of handle portion 110, whereupon third steering cable 158 exits introducer sheath 130 via opening 1963 that is located near the terminal portion of introducer sheath 130 (i.e., the portion that is located inside of handle portion 110). In this way, the distal end of third steering cable 158 is able to pass out of steering lumen 150 and become affixed to externally-threaded stem 188, which is accomplished by passing third steering cable 158 through axial bore 1963 in flange 400 that extends from the proximal end of externally-threaded stem 188, and affixing third steering cable 158 after it has exited from the distal end of axial bore 1963. Likewise, for embodiments of the steerable introducer sheath assembly of the present disclosure that include an introducer sheath similar to introducer sheath 1300 that is shown in FIG. 3B, the distal end of third steering cable 1580 passes out of steering cable lumen 1500 and exits introducer sheath 1300 via an opening that is essentially identical to opening 1963 that is shown in FIG. 2D and discussed above. Once it has passed out of introducer sheath 1300, third steering cable 1580 may be affixed to externally-threaded stem 188 by passing it through axial bore 1963 in flange 400 that extends from the proximal end of externally-threaded stem 188, and affixing third steering cable 1580 after it has exited from the distal end of axial bore 1963.

As best illustrated in FIGS. 2A, and 2D, when an operator views sheath assembly 100 from the proximal handle portion 110 and looking distally along introducer sheath 130 as it extends outwardly in an undeflected position, rotation of distal end cap 180 in a clockwise direction causes the correspondingly-threaded stem 188 to move in a proximal direction (i.e. towards the interior of handle portion 110, as best shown in FIG. 2D, top), which increases the amount of tension placed on third steering cable 158, and thereby causes an increase in the "vertical" curvature of the distal portion 132 of introducer sheath 130. Conversely, rotation of distal end cap 180 in a counterclockwise direction causes externally-threaded stem 188 to move in a distal fashion (i.e. away from the interior of handle portion 110, as best shown in FIG. 2D, bottom), which reduces the amount of tension present in third steering cable 158, and reduces the amount of "vertical" curvature present in distal portion 132 of introducer sheath 130. This "vertical" curvature of distal portion 136 of introducer sheath 130 can be seen in FIG. 1D (depicting a steerable introducer sheath as viewed from the "right hand" side), which illustrates how distal portion (136) of introducer sheath 130 extends in a parallel direction to longitudinal center axis 102 when distal cap 180 has been rotated such that externally-threaded stem 188 places no tension on steering cable 158 (FIG. 1D, at center), and how distal portion (136) of introducer sheath 130 becomes more "vertically" curved in a direction that is elevated with respect to longitudinal center axis 102 (FIG. 1D, at left) when distal end cap 180 has been rotated so as to cause externally-threaded stem 188 to move in a proximal fashion and increase the tension on steering cable 158. A "self-locking" functionality that preserves the desired "vertical" curvature may be provided by configuring the threaded portions of distal end cap 180 and externally-threaded stem 188 to interact with sufficient friction that when a user ceases rotation of distal end cap 180, externally-threaded stem 188 remains fixed in its position, thereby maintaining the tension in third steering cable 158, and preserving the desired "vertical" curvature to distal portion 132 of introducer sheath 130.

In certain embodiments of the introducer sheath assembly of the present disclosure, the engagement between end cap 180 and externally-threaded stem 188 may be used to modulate the "vertical" curvature of an introducer sheath that is similar to introducer sheath 1300 that is depicted in FIG. 3B. In these embodiments, the proximal/distal movement of externally-threaded stem 188 is utilized (directly or indirectly) to selectively increase or decrease the relative tension in third and fourth steering cables 1580 and 1520, thereby modifying the "vertical" curvature of distal portion 1360 of introducer sheath 1300 in the direction of vertical axis 103 (i.e., above or below the horizontal plane). This "vertical" curvature of distal portion 136 of introducer sheath 130 can be seen in FIG. 1D (depicting a steerable introducer sheath as viewed from the "right hand" side), which illustrates how distal portion (1360) of introducer sheath 1300 extends in a parallel direction to longitudinal center axis 102 when distal cap 180 has been rotated such that externally-threaded stem 188 places no tension on third and fourth steering cables 1580 and 1520 (FIG. 1D, at center), how distal portion (1360) of introducer sheath 1300 becomes more "vertically" curved in a direction that is elevated with respect to longitudinal center axis 102 (FIG. 1D, at left) when distal end cap 180 has been rotated so as to cause externally-threaded stem 188 to move in a fashion that increases the tension on third steering cable 1580 and decreases the tension on fourth steering cable 1520 (FIG. 1D, at left), and how distal portion (1360) of introducer sheath 1300 becomes more "vertically" curved in a direction that is depressed with respect to longitudinal center axis 102 (FIG. 1D, at right) when distal end cap 180 has been rotated so as to cause externally-threaded stem 188 to move in a fashion that increases the decreases the tension on third steering cable 1580 and increases the tension on fourth steering cable 1520.

Certain embodiments of the steerable introducer sheath assembly may include both a "horizontal" steering lever for modulating the amount of "horizontal" curvature present in the distal portion of the introducer sheath (as described above and depicted in FIGS. 1A-1D and 2A, and a "vertical" steering lever for modulating the amount of "vertical" curvature present in distal portion 132 of introducer sheath 130. In such "dual lever" embodiments, the use of a "vertical" steering lever instead of the distal end cap and externally-threaded stem assembly described above for controlling "vertical" curvature provides uniformity with respect to the mechanisms for altering the curvature of the introducer sheath (i.e., the same type of mechanism—a steering lever—is used to modify both "vertical" and "horizontal" curvature).

Figure 6A:
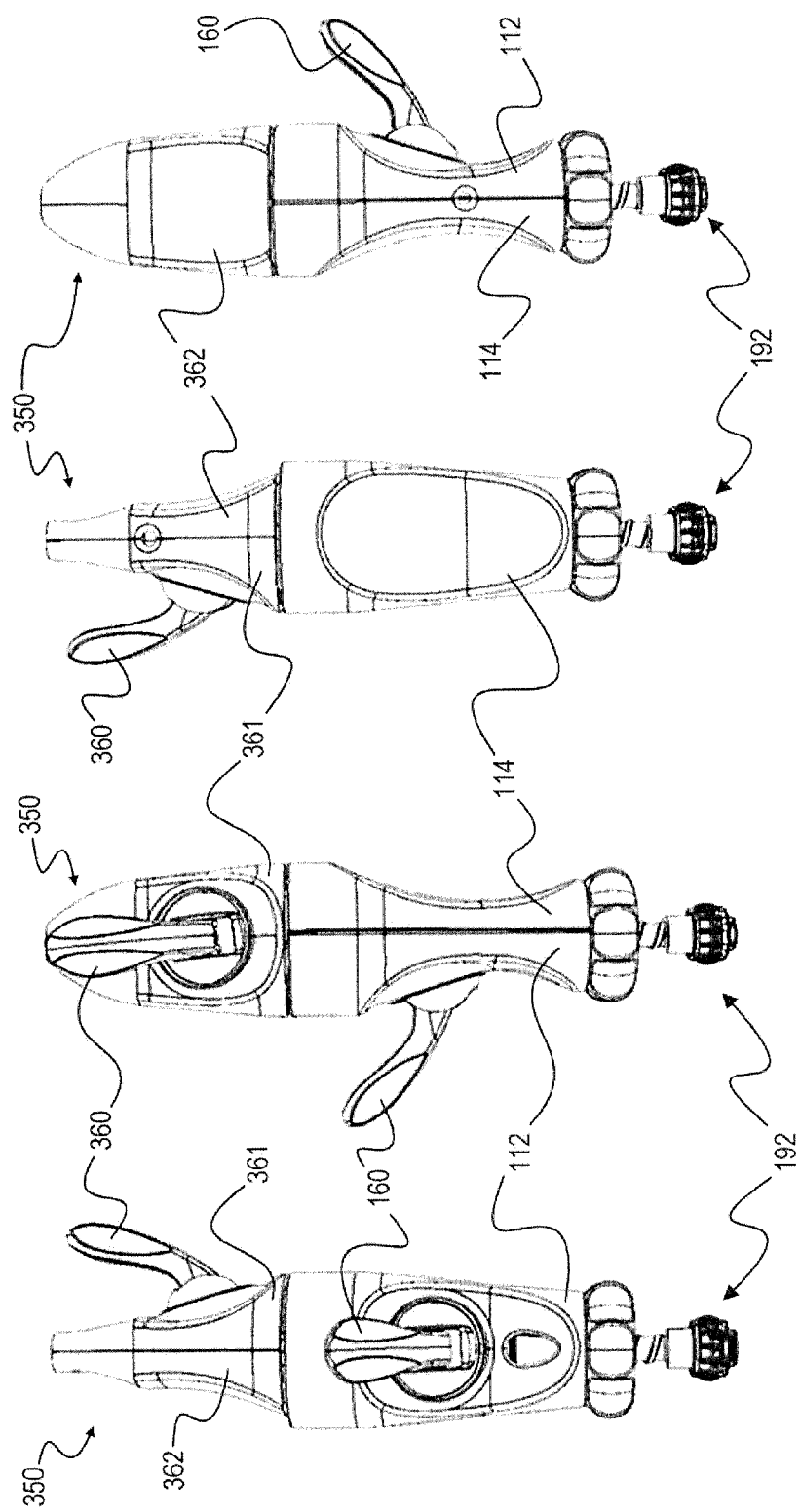
FIG. 6A provides top, bottom, and side views of the handle portion of a steerable introducer sheath assembly in accordance with an embodiment of the present disclosure.
Figure 6B:
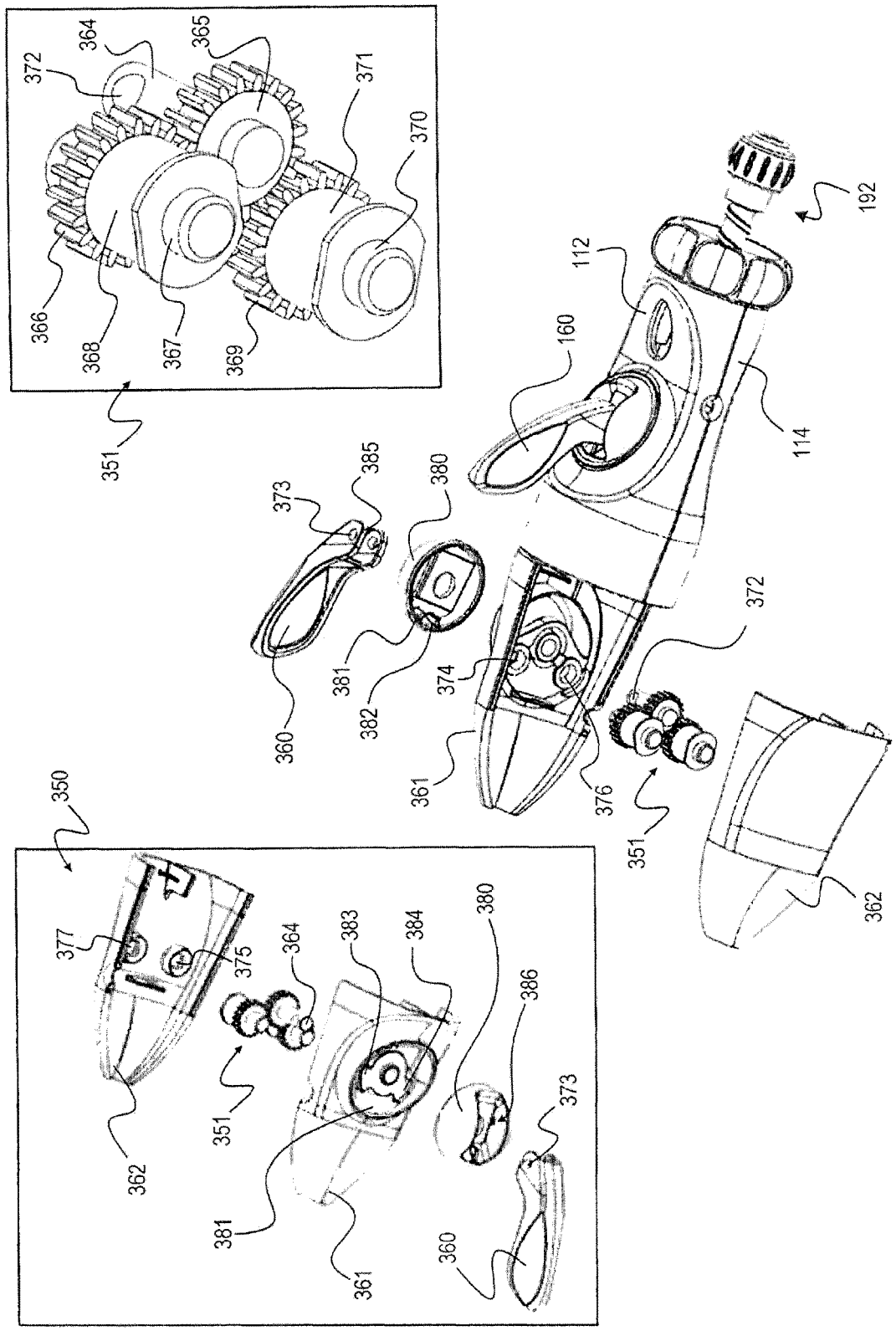
FIG. 6B provides perspective views of a handle of a steerable introducer sheath assembly in accordance with an embodiment of the present disclosure, with elements of the distal housing portion separated to aid visualization of certain features.
Figure 6C:
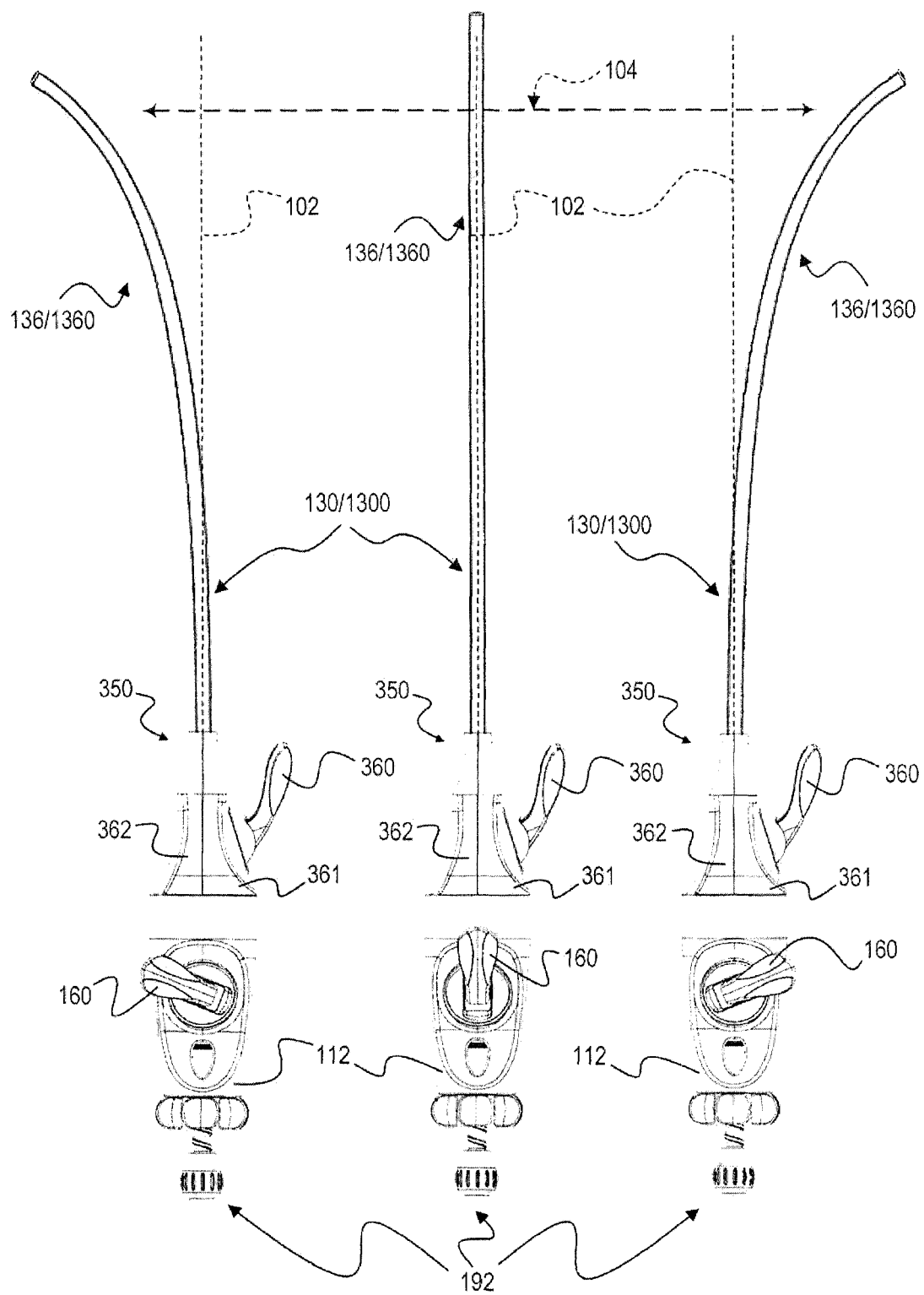
FIG. 6C provides top views of a steerable introducer sheath assembly in accordance with an embodiment of the present disclosure.
Figure 6D:
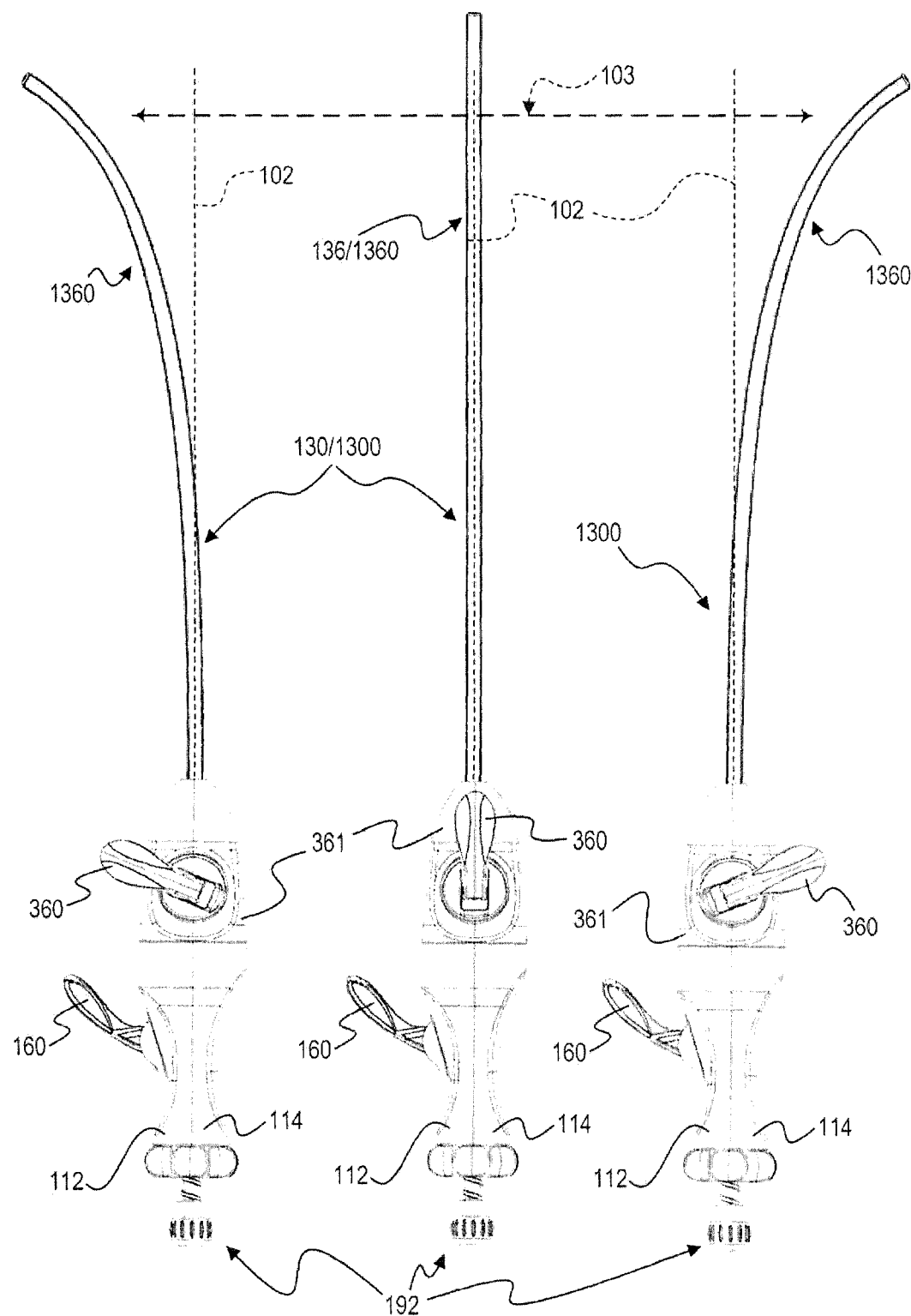
FIG. 6D provides side views of a steerable introducer sheath assembly in accordance with an embodiment of the present disclosure.

For example, as shown in FIGS. 6A-6D, the distal end cap 180 and its associated components (externally-threaded stem 188, torque transmission lock 1900, transmission lock cap 1903, and thrust bearing washer 1905) from the steerable introducer sheath assembly depicted in FIGS. 1A-1C and 4A-4B may be replaced with a distal housing assembly 350, which as best shown in FIG. 6B includes distal housing portions 361 and 362 that together house a vertical steering assembly 351 that is articulated by vertical steering lever 360. As best shown in FIG. 6B, vertical steering lever 360 is non-rotatably secured to a first end of steering post 364 by way of bores that align to receive a retaining pin. Steering post 364, in turn, passes through distal housing portion 361 and is non-rotatably secured to main vertical drive gear 365 at its second end. Main vertical drive gear 365 is situated within distal housing assembly 350 so that is capable of simultaneously engaging and rotating both upper vertical drive gear 366 and lower vertical drive gear 369. Upper vertical drive gear 366 is non-rotatably secured to upper rotatable post 367, which extends inwardly from housings 374 and 375 on the interior of distal housing portions 361 and 362 (respectively), with upper rotatable post 367 further being non-rotatably secured to upper barrel portion 368. Lower vertical drive gear 369 is non-rotatably secured to lower rotatable post 370, which extends inwardly from housings 376 and 377 on the interior of distal housing portions 361 and 362 (respectively), with lower rotatable post 370 further being non-rotatably secured to lower barrel portion 371.

In certain embodiments of the steerable introducer sheath assembly of the present disclosure, a vertical steering lever and associated elements described above may be provided in combination with an introducer sheath that is similar to introducer sheath 1300 that is depicted in FIG. 3B. In these embodiments, third and fourth steering cables 1580 and 1520 are affixed at or near the distal tip 1360 of introducer sheath 1300, with the cables themselves extending proximally through lumens 1500 and 1420 (respectively) until the proximal ends terminate in the interior of handle portion 110, whereupon the proximal ends of third and fourth steering cables 1580 and 1520 pass out of steering cable lumens 1500 and 1420 (respectively) and exit introducer sheath 1300 via similar openings to those openings (1960 and 1961) depicted in FIG. 2A, and become engaged with one or more steering mechanisms that are capable of selectively increasing or decreasing the tension in third and fourth steering cables 1580 and 1520.

In these embodiments, the proximal end of third steering cable 1580 is affixed to upper barrel portion 368, and the proximal end of fourth steering cable 1520 is affixed to lower barrel portion 371. Rotation of vertical steering lever 360 causes main vertical drive gear 365 to simultaneously engage with and rotate upper and lower vertical drive gears 366 and 369, and their associated upper and lower barrel portions 368 and 371. This in turn causes third steering cable 1580 and fourth steering cable 1520 to become coiled about lower barrel portions 368 and 371, respectively, so that as the tension in third steering cable 1580 becomes increased, the tension in fourth steering cable 1520 becomes decreased, and vice versa. As such, third and fourth steering cables 1580 and 1520 work in unison to either increase or decrease the "vertical" curvature of distal portion 1320 of introducer sheath 1300 in a direction that is either elevated above or depressed below the horizontal plane.

For example, in certain embodiments, first and second steering cables 1580 and 1520 may be affixed to and engaged by their respective upper and lower barrel portions 368 and 371 in such a manner that, as best illustrated in FIG. 6D (providing views of a "two lever" steerable introducer sheath viewed from the "right hand" side), the rotation of steering lever 360 in a counterclockwise fashion (i.e., so that the distal end of steering lever 360 is pointing in a direction that is elevated relative to longitudinal center axis 102) causes the distal portion (1360) of introducer sheath 1300 to "vertically" curve in an elevated fashion with respect to longitudinal center axis 102 (FIG. 6D, at left), turning steering lever 360 in a clockwise fashion (i.e. so that the distal end of steering lever 360 is pointing in a direction that is depressed relative to longitudinal center axis 102) causes the distal portion (1360) of introducer sheath 1300 to "vertically" curve in a depressed fashion with respect to longitudinal center axis 102 (FIG. 6D, at bottom), and returning steering lever 160 to the center position (i.e. so that the distal end of steering lever 360 points in a parallel direction to longitudinal center axis 102) causes distal portion (1360) of introducer sheath 1300 to extend in a parallel direction to longitudinal center axis 102 (i.e. with no "horizontal" curvature, as in FIG. 6D, at center). In this fashion, the orientation of the distal end of steering lever 360 may provide the user with an indication as to the presence, directionality, and relative extent of any "horizontal" curvature that has been introduced to the distal portion (1360) of introducer sheath 1300.

In alternative embodiments, third and fourth steering cables 1580 and 1520 may be affixed to and engaged by barrel portions 368 and 371, respectively, such that turning vertical steering lever 360 in a "clockwise" fashion will cause the distal portion (1360) of introducer sheath 1300 to "vertically" curve above longitudinal center axis 102, and vice versa.

In certain embodiments of the introducer sheath assembly of the present disclosure, a vertical steering lever and certain associated elements similar to those described above may be provided in combination with an introducer sheath that is similar to introducer sheath 130 that is depicted in FIG. 3A. For example, the vertical steering lever may be secured to a first end of a rotatable post that extends through the surface of distal handle assembly 350 and terminates internally in a similar fashion to that which is shown in FIG. 6B with respect to vertical steering lever 360 and rotatable post 364. The distal end of third steering cable 158 from introducer sheath 130 is (directly or indirectly) affixed to and engaged by rotatable post 364 so that when steering lever 360 is rotated as described above, the resulting axial rotation of rotatable post 364 causes the proximal end of third steering cable 158 to become either coiled or uncoiled from around the barrel portion of rotatable post 364. As third steering cable 158 becomes more coiled around the barrel portion of rotatable post 364, the tension placed on third steering cable 158 is increased, and the amount of "vertical" curvature present in distal portion 132 of the introducer sheath is likewise increased. Conversely, as third steering cable 158 becomes less coiled around the barrel portion of rotatable post 364, the tension placed on third steering cable 158 is decreased, and the amount of curvature present in distal portion 132 of introducer sheath 130 is likewise reduced. For example, in certain embodiments third steering cable 158 may be affixed to and engaged by rotatable post 364 in such a manner that, as best illustrated in FIG. 6D (providing views of a "two lever" steerable introducer sheath viewed from the "right hand" side), the rotation of steering lever 360 in a counterclockwise fashion (i.e., so that the distal end of steering lever 360 is elevated relative to longitudinal center axis 102) causes the distal portion (1360) of introducer sheath 1300 to "vertically" curve above longitudinal center axis 102 (FIG. 6D, at left), and returning steering lever 160 to the center position (i.e. so that the distal end of steering lever 360 points in a parallel direction to longitudinal center axis 102) causes distal portion (1360) of introducer sheath 1300 to revert to extending in a direction that is parallel to longitudinal center axis 102 (i.e. with no "vertical" curvature, as in FIG. 6D, at center). Here again, the orientation of the distal end of steering lever 360 provides an indication as to the presence, directionality, and relative extent of any "vertical" curvature that has been introduced to the distal portion (1360) of introducer sheath 1300.

In certain embodiments of the steerable introducer sheath assembly in accordance with the present disclosure, the interactions between the vertical steering lever and associated steering gear assemblies such as those described above for vertical steering lever 360 may modified to either increase or decrease the "vertical sensitivity" of the vertical steering lever (i.e. the extent to which "vertical" curvature is modified when the vertical steering lever is rotated to a particular degree). For example, in certain embodiments a variable transmission may be provided that allows the user to modulate the "vertical sensitivity" by selectively modifying the gearing ratios between the drive gear and any associated gear assemblies (for example, allowing the user to modify the respective gear ratios contained within vertical steering assembly 351 that is shown in FIG. 6B). Alternatively, spring-loaded gear posts and/or flywheel assemblies may be provided for modulating the sensitivity of the vertical steering lever and associated steering assemblies.

Embodiments of the steerable introducer sheath assembly that provide a vertical steering lever for controlling "vertical curvature" (as detailed above) may further include a mechanism for locking the vertical steering lever in place once a desired amount of curvature has been achieved for the introducer sheath. As shown in FIG. 6B, for example, distal handle assembly 350 may be configured with a vertical steering lever 360 that includes a camming surface 385, such that when steering lever 360 is rotated upwardly about the steering lever pin that joins it to steering post 364, the camming surface becomes frictionally engaged with exterior face of the upper portion (361) of distal handle assembly 350, and steering post 364 (or an associated element) likewise becomes frictionally engaged with the interior face of the upper portion (361) of distal handle assembly 350. This "locking engagement" is essentially the same as that which is depicted in FIGS. 5A and 5B, which depict horizontal steering handle 160 in an "unlocked" position (FIG. 5A) and a "locked" position (FIG. 5B). In certain embodiments, this "locking" friction may be modulated by providing one or more washers (for example, the wave spring washers (1915) depicted in FIGS. 5A and 5B) to mediate the frictional engagement with the interior and exterior faces of the upper portion (361) of distal handle assembly 350.

Referring again to FIG. 6B, embodiments of the steerable introducer sheath assembly that provide a vertical steering lever for controlling "vertical" curvature may further include a vertical steering lever dome cover 380 that sits within a vertical dome cover recess 381 extruding from the exterior face of the upper portion (361) of distal handle assembly 350, and thereby mediating the interaction between camming surface 385 of vertical steering lever 360, and the outer face of upper handle portion 361. As best shown in FIG. 6B (left inset), vertical steering lever dome cover 380 may be shaped to provide a central slot 386 through which steering lever 360 protrudes as shown in FIGS. 6A and 6D, with central slot 386 of sufficient width to accommodate vertical rotation of vertical steering lever 360 between the "unlocked" and "locked" positions, while also providing lateral support for steering lever 360 when it is manipulated to turn steering post 364, and further ensuring that when pivoted from the "unlocked" position to the "locked" position (FIG. 5B), steering lever 360 is constrained to a direction that is perpendicular to the line of axis of the steering lever pin that joins it to steering post 364.

Referring again to FIG. 6B, embodiments of the steerable introducer sheath assembly that provide a vertical steering lever for controlling "vertical" curvature, vertical dome cover 380 and vertical dome cover recess 381 may be configured to limit the angular displacement of steering post 364 about its longitudinal axis when vertical steering lever 360 is manipulated. For example, as best shown in FIG. 6B, this may be achieved through flanges (381 and 382) that extend from the underside of vertical dome cover 380, and interact with the distal faces formed by corresponding protrusions exemplified in FIG. 6B (left inset) as 383 and 384 to constrain the rotation of steering lever 360. This protects third steering cable 1580 and/or fourth steering cable 1520 from the excessive strain that could result from a user's attempt to overtighten them using steering lever 360. In certain embodiments, protrusions 383 and 384 and/or flanges 381 and 382 may be adjustable, so that the extent to which the rotation of steering lever 360 is constrained can be modified according to the user's preferences.

As discussed above, first and second steering cables 154 and 156 work in unison to effect the curvature of distal portion 132 of introducer sheath 130, with first and second gear assemblies 168 and 174 being simultaneously engaged by drive gear 166 so that when the operator manipulates steering lever 160 to increase the tension in steering cable 154, the tension in steering cable 156 is lessened by the same amount, and vice versa. The simultaneous operation of gear assemblies 168 and 174 prevents slack from building up in either of first and second steering cables 154 and 156 when the user manipulates steering lever 160 to effect "horizontal" curvature of distal portion 132 of introducer sheath 130. This is also true with respect to introducer sheath 1300 that is depicted in FIG. 3B, where the introduction of "horizontal" curvature to distal portion 1320 of introducer sheath 1300 through manipulation of steering lever 160 likewise does not lead to slack buildup in first and second steering cables 1540 and 1560, because as tension in one of the steering cables increases, the tension in the other steering cable decreases, and vice versa.

However, when a user increases the "vertical" curvature of distal portion 132 of introducer sheath 130 by increasing the tension of third steering cable 158, this may in turn cause slack to build up in first steering cable 154 and/or second steering cable 156. Likewise, when a user modifies the "vertical" curvature of distal portion 1320 of introducer sheath 1300 (in a direction that is either elevated or depressed with respect to the horizontal plane) by modulating the tension of third and fourth steering cables 1580 and 1520, this may in turn cause slack to build up in first steering cable 1540 and/or second steering cable 1560. This accumulation of slack may cause an operator to experience an undesirably delayed response when attempting to utilize a horizontal steering lever (e.g., steering lever 160 described above) to vary the tension in first and/or second steering cables 154 and 156 (or first and/or second steering cables 1520 and 1580) so as to modulate the "horizontal" curvature of distal portion 132 of introducer sheath 130 (or distal portion 1320 of introducer sheath 1300). To prevent this, steerable introducer sheath assemblies of the present disclosure may include a mechanism for removing such slack.

Figure 7A:
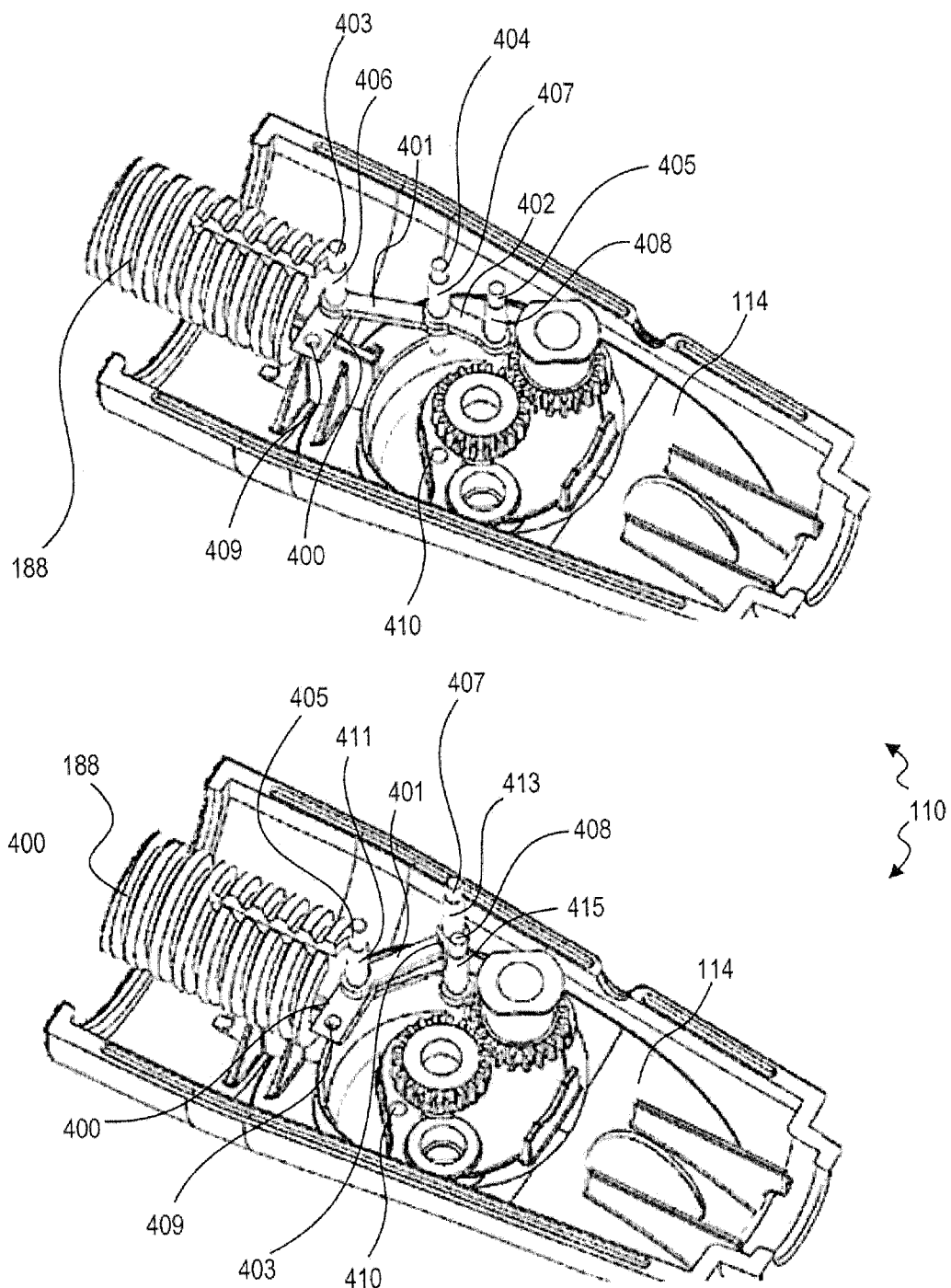
FIG. 7A provides perspective views of the handle portion of a steerable introducer sheath assembly in accordance with an embodiment of the present disclosure, with a portion of the handle housing removed to permit visualization of a slack elimination assembly in both a resting configuration (top image) and a slack-removing configuration (bottom image)
Figure 7B:
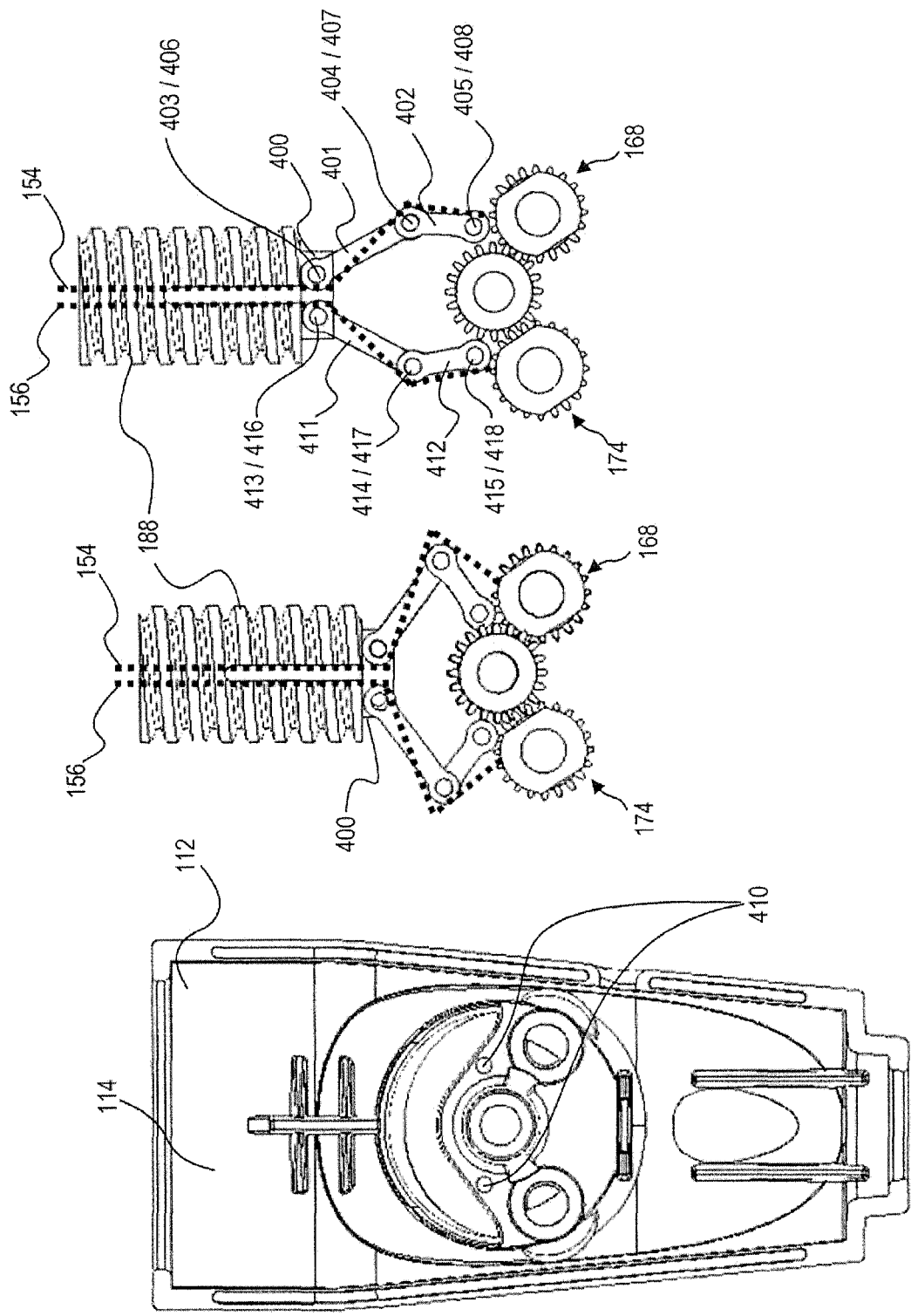
FIG. 7B provides isolated views of an upper handle portion (left), an isolated slack elimination assembly in a slack-removing configuration (middle) and an isolated slack elimination assembly in a resting configuration (right), in accordance with an embodiment of the present disclosure.

For example, as shown in FIGS. 7A and 7B, externally-threaded stem 188 may feature a proximally-extending linkage flange 400 by which the axial movement of externally-threaded stem 188 is transferred to a first slack removal assembly comprising first connecting arm 401, second connecting arm 402, flange linking post 403 with associated bearing cylinder 406, connecting arm linking post 404 with associated bearing cylinder 407, and connecting arm retaining post 405 with associated bearing cylinder 408. More specifically as best shown in FIG. 7B, linkage flange 400 is joined to the distal end of first connecting arm 401 by way of overlapping openings that receive flange linking post 403; the proximal end of first connecting arm 401 is joined to the distal end of second connecting arm 402 by way of overlapping openings that receive connecting arm linking post 404; and the proximal end of second connecting arm 402 contains an opening through which one end of connecting arm retaining post 405 is passed and then seated in connecting arm retaining post receptacle 410 on the interior of lower housing portion 114. First steering cable 154 is threaded through this slack removal assembly as shown by the dotted line in FIG. 7B, with bearing cylinders 406-408 configured to act as rollers that rotate freely about respective posts 403-405, to minimizing friction with steering cable 154. As further shown in FIG. 7B, second linking cable 156 is threaded through a second slack removal assembly that is likewise coupled to linking flange 400, with the second slack removal assembly comprising first connecting arm 411, second connecting arm 412, flange linking post 413 with associated bearing cylinder 416, connecting arm linking post 414 with associated bearing cylinder 417, and connecting arm retaining post 415 with associated bearing cylinder 418, and these components joined together as described above with respect to the first slack removal assembly.

As best shown in FIG. 7B, as externally-threaded stem 188 is advanced in a distal direction, the interaction between linking flange 400 and the slack removal assembly causes posts 403-405 and 413-415 (and associated bearings 406-408 and 416-418) to become aligned in a more linear fashion, which in turn allows steering cables 154 and 156 to travel along a shorter path from their distal affixation points within introducer sheath 130 to their proximal affixation points at gear assemblies 168 and 174. Conversely, as externally-threaded stem 188 is advanced in a more proximal direction, the interaction between linking flange 400 and the slack removal assembly causes posts 403-405 and 413-415 (and associated bearings 406-408 and 416-418) to become aligned in a more triangular configuration, with connecting arm linking posts 404 and 414 situated considerably more towards the exterior of handle 110 than flange linking posts 403 and 413, and connecting arm retaining posts 405 and 415. This triangular configuration removes excess slack from steering cables 154 and 156 by causing them to travel along a longer path from their distal affixation points within introducer sheath 130 to their proximal affixation points at gear assemblies 168 and 174. Thus, when externally-threaded stem 188 is advanced in a proximal direction that increases the tension on third steering cable 158 (which in turn increases "vertical" curvature that could cause steering cables 154 and 156 to become slackened), the slack removal assembly described above shifts into a triangular configuration that removes excess slack by increasing the distance traveled by cables 154 and 156 from their proximal gear assemblies to the distal tip of introducer sheath 130.

Likewise, for those embodiments in which a "vertical" steering lever 360 is used (i) in connection with introducer sheath 1300 that is depicted in FIG. 3B, where the vertical steering lever 360 is rotated to modulate the "vertical" curvature of distal portion 1320 of introducer sheath 1300 (as discussed above and best illustrated in FIGS. 6B and 6D), or (ii) in connection with introducer sheath 130 that is depicted in FIG. 3A, whereby the vertical steering lever 360 is rotated to modulate the "vertical" curvature of distal portion 132 of introducer sheath 130 (as discussed above and best illustrated in FIGS. 6B and 6C) the potential introduction of slack into first and/or second steering cables 1520 and 1580 (from introducer sheath 1300), or first and/or second steering cables 154 and 156 (from introducer sheath 130) may be addressed by coupling the rotation of steering post 364 to the slack removal assembly. For example, one or more coupling rods or cables may be provided to couple steering post 364 to the slack removal assembly such that when a user increases the tension in third steering cable 158 by rotating steering post 364 using "vertical" steering lever 360 (thereby increasing the "vertical" curvature of distal portion 132 of introducer sheath 130), the coupling rods or cables cause the slack removal assembly to become aligned in the "triangular" configuration that, as discussed above and shown in FIG. 7B, acts to remove excess slack from steering cables 154 and 156 by causing them to travel along a longer path from their affixation points at the distal tip of introducer sheath 130 to their proximal affixation points at gear assemblies 168 and 174. Conversely, when a user increases the tension in third steering cable 158 by rotating steering post 364 using "vertical" steering lever 360 (thereby reducing or eliminating any "vertical" curvature of distal portion 132 of introducer sheath 130), the coupling rods or cables cause the slack removal assembly to become aligned in the more linear fashion that, as discussed above and shown in FIG. 7B, allows steering cables 154 and 156 to travel along a shorter path from their distal affixation points within introducer sheath 130 to their proximal affixation points at gear assemblies 168 and 174.

Steerable introducer sheath assemblies in accordance with the present disclosure may also include a device locking assembly that allows user to selectively fix a catheterized instrument within the introducer sheath after it has been advanced (or retracted) to the desired extent, and to further exert fine control over the advancement or retraction of a catheterized instrument that has been so affixed. Such catheterized instruments may include, for example, dilator through which standard length Bayliss RF transseptal devices (available from Bayliss Medical, Montreal, Canada), Brockenbrough transseptal needles, or other similar instruments may be introduced. As can be seen in FIGS. 1A, and 8A-8D, for example, such a device locking assembly may be disposed within the proximal aperture 124 (best shown in FIGS. 8B and 8C) that is formed when the proximal faces of upper housing portion 112 and a lower housing portion 114 are joined together to form handle portion 110. As further shown in FIGS. 8A-8D, the device locking assembly may include a device locking stem (shown as 191*a* in FIGS. 8A-8C and as 191*b* in FIG. 8D) that passes through the proximal face of handle portion 110, with said device locking stem containing a smooth central bore (199) through which an instrument for catheterization may be passed and inserted into the steerable introducer sheath (130, 1300), and said device locking stem being further configured to variably affix said instrument for catheterization in an immovable fashion. For example, as can best be seen from the depictions of device locking stem 191*a* that are shown in FIGS. 8B and 8C, in certain embodiments the device locking stem may be externally threaded at its proximal end to receive a hemostatic valve cap (196*a*) through which an instrument for catheterization is passed as it is inserted into central bore 199 of the device locking stem, thereby allowing a user to selectively affix said instrument for catheterization in an immovable fashion within device locking stem 191a by tightening or un-tightening hemostatic valve cap 196a. Alternatively, as can best be seen from the depictions of device locking stem 191b that is shown in FIG. 8D, in certain embodiments the device locking stem may define a distal collet 194 with smooth outer surfaces, allowing a user to selectively affix said instrument for catheterization in an immovable fashion within device locking stem 191b by means of sliding lock knob 196b, which defines a smooth frustoconical bore 181 that engages with and compresses collet 194 inwardly so that it tightens about said instrument for catheterization (which in FIG. 8D is represented by dilator 159).

Figure 8E:
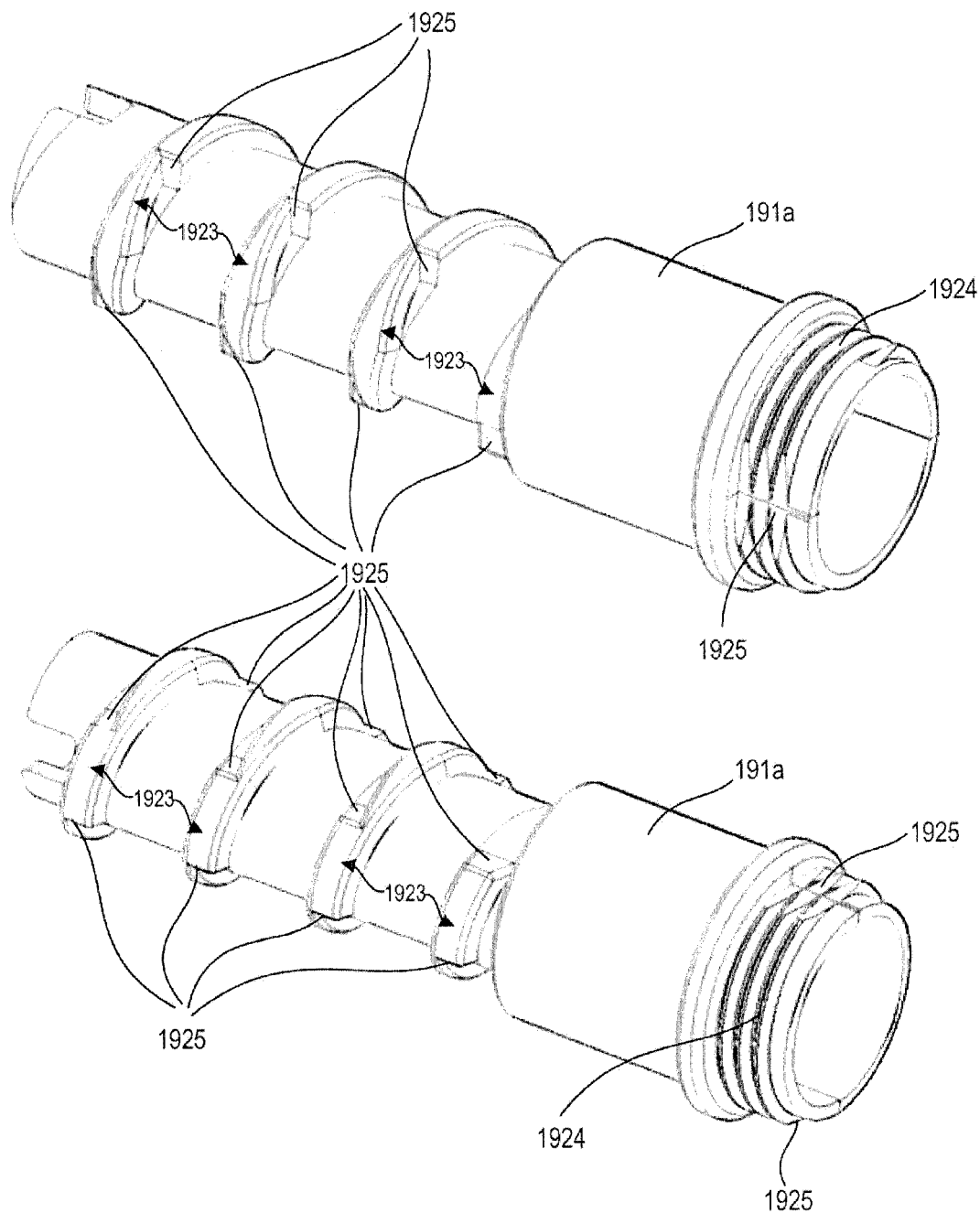
FIG. 8E provides perspective views of a device locking stem from the handle portion of a steerable introducer sheath assembly in accordance with an embodiment of the present disclosure.

In certain embodiments, further control over the advancement (or retraction) of an instrument for catheterization (for example dilator 159 shown in FIGS. 8A and 8D) may be provided by configuring device locking stem (191a, 191b) to be mechanically advanced (or retracted) through the proximal face of handle portion 110 after the instrument for catheterization has been affixed in an immovable fashion as described above. For example, as best illustrated in FIGS. 8A-8C (showing device locking stem 191a) and FIG. 8D (showing device locking stem 191b), the device locking stem may be configured with external threads 1923 that engage with a correspondingly threaded bore (197) that passes through an advance knob (195). The external threads on device locking stem (191a, 191b) (including both the external threads that engage with threaded bore 197, and the external threads at the proximal end of device locking stem 191a that engage hemostatic valve cap 196a) may be either continuous (i.e., "carried through") or, as best shown in FIG. 8E (depicting device locking stem 191a), include interrupting "flats" 1925 situated along the length of the externally threaded areas to facilitate the use of injection molding manufacturing techniques.

Referring again to FIGS. 8A-8D, the advance knob may be rotatably received and retained within proximal aperture 124 of handle portion 110 by a retention flange that extends radially from the distal portion of advance knob 195 with a greater diameter than proximal aperture 124. This radially-extending retention flange may be either continuous or discontinuous. For example, FIG. 8D shows an advance knob 195 with a continuous retention flange (193b). Alternatively, FIG. 2C shows proximal, side perspective, and distal views of an advance knob 195 with a discontinuous retention flange comprising outwardly depending tabs 1926 that together define a flange with a radius that is greater than that of proximal aperture 124, thereby ensuring that advance knob 195 is axially retained within handle portion 110 (as can best be seen in FIGS. 2D and 9A). As can best be seen in FIG. 2C, where the advance knob (195) has a discontinuous retention flange, it may also include a plurality of vents 1927 that pass through the proximal face of advance knob 195, which correspond to outwardly depending tabs 1926, and are sized and situated to facilitate the use of injection molding techniques to manufacture the advance knob.

Figure 9A:
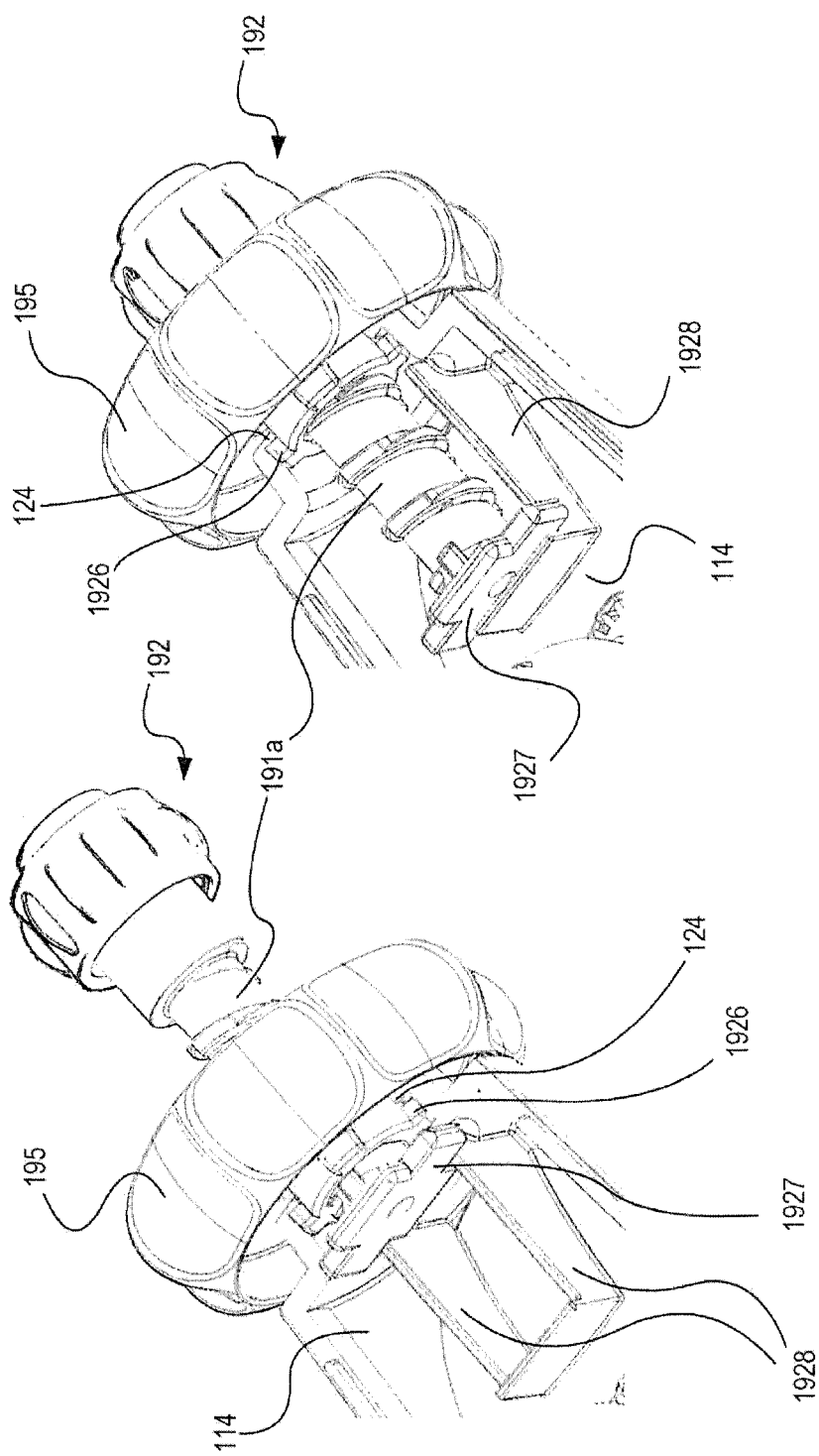
FIG. 9A provides detailed views of the distal end of a steerable introducer sheath assembly in accordance with an embodiment of the present disclosure, with a portion of the handle housing removed to permit visualization of interior elements.

As best shown in FIG. 9A, rotation of advance knob 195 causes device locking stem (191a, 191b) to move in either a proximal direction (i.e. towards the user, as shown in FIG. 9A, at left), or a distal direction (i.e. away from the user and into handle portion 110, as shown in FIG. 9A, at right). In certain embodiments, device locking stem (191a, 191b) and advance knob 195 may be threaded such that rotation of advance knob 195 in a counterclockwise fashion causes device locking stem (191a, 191b) to move in a proximal direction, and rotation of advance knob 195 in a clockwise fashion causes device locking stem (191a, 191b) to move in a distal direction; in other embodiments the threading may be configured so that rotation of the advance knob in a clockwise fashion causes the device locking stem to move in a proximal direction, and rotation of the advance knob in a counterclockwise fashion causes the device locking stem to move in a proximal direction. Thus, after engaging device lock assembly 192 (which for the device locking stem 191a shown in FIG. 9A would require tightening hemostatic valve cap 196a) to affix the instrument for catheterization (for example the dilator (159) shown in FIGS. 8A and 8D), the user may exercise precise control over advancement of the instrument for catheterization's distal tip by rotating advance knob 195, thereby causing the device locking stem (and axially-affixed instrument for catheterization) to move in either a distal fashion (extending the instrument towards and/or through the distal tip of the introducer sheath), or a proximal fashion (withdrawing the dilator back through and/or away from the distal tip of introducer sheath). This in turn facilitates the performance of delicate operations (such as puncturing the interatrial septum) in a very controlled manner.

Figure 9B:
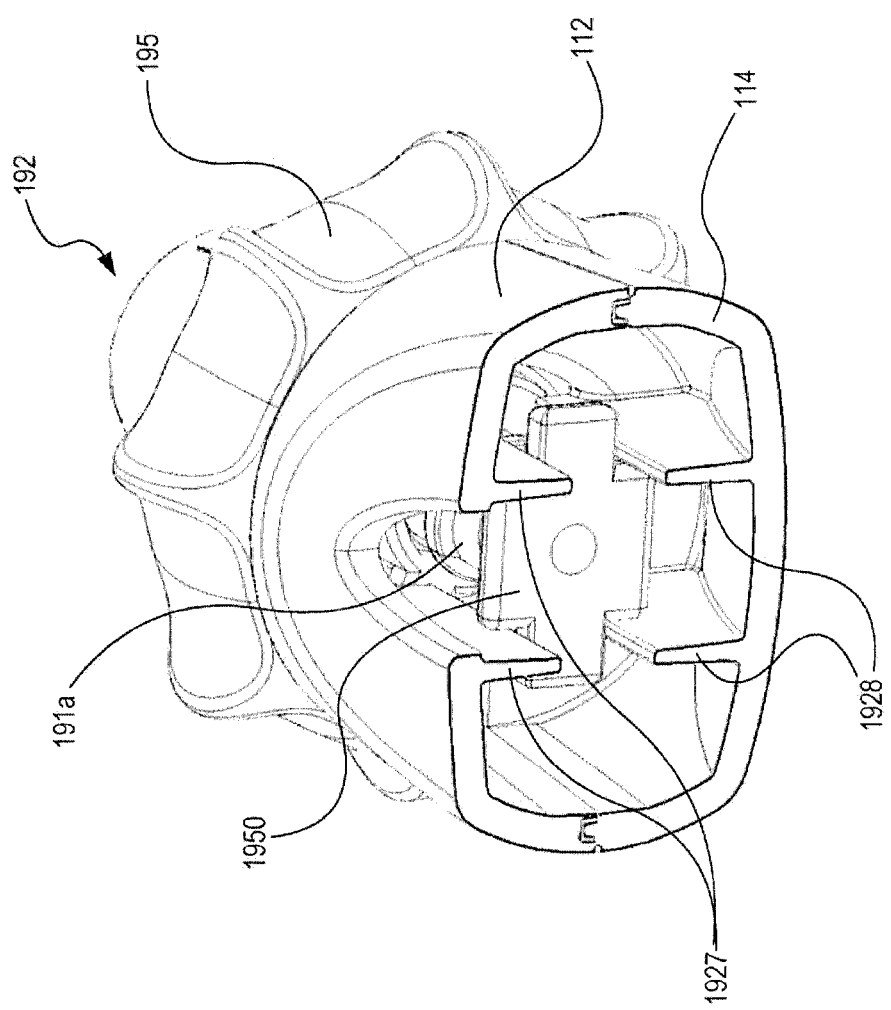
FIG. 9B is a cross-sectional view of the proximal end of the handle portion of a steerable introducer sheath assembly in accordance with an embodiment of the present disclosure, as viewed from a distal perspective.
Figure 9C:
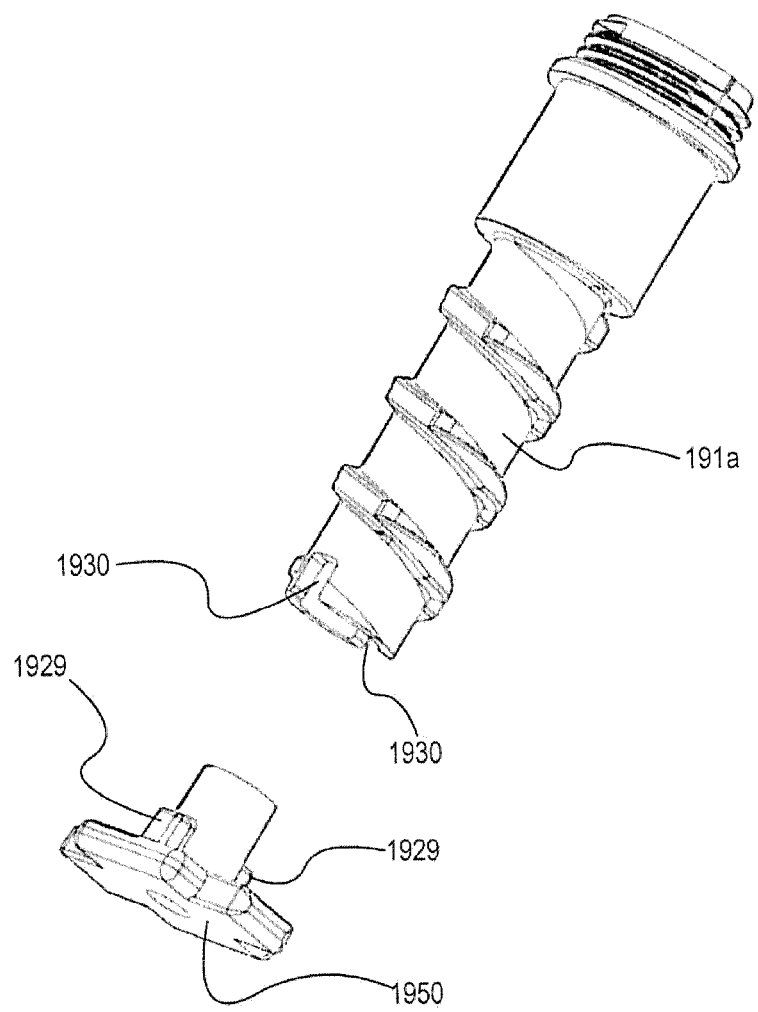
FIG. 9C is a top perspective view of the sites of engagement between a device locking stem and an internal guide component for use with a steerable introducer sheath assembly in accordance with an embodiment of the present disclosure.

The steerable introducer sheath assembly may also include an internal guide to prevent the device locking stem from instead being improperly rotated about axis 102 along with advance knob 195 when it is rotated, which in turn ensures that the device locking stem moves in a proper distal or proximal fashion along axis 102 when the user manipulates advance knob 195. As best shown in FIGS. 9A and 9C, for example, internal guide 1950 may comprise a flat, cruciform distal base with a central bore that is defined by a hollow columnar stem extending in a proximal direction. As best shown in FIG. 9B, the cruciform base of internal guide 1950 causes it to be seated in a rotationally-fixed manner within a guide channel that is defined by a set of parallel flanges 1927 that extend inwardly from the inner face of upper handle portion 112, and a corresponding set of parallel flanges 1928 that extend inwardly from the inner face of lower handle portion 114. The proximal end of internal guide 1950 is further configured to engage the device locking stem in a rotationally-fixed manner. For example, as best shown in FIG. 9C, the engagement between internal guide 1950 and the device locking stem may be mediated by one or more indentations (1930) shown at the distal end of locking stem 191a, which engage in a rotationally-fixed manner with one or more flanking bosses 1929 that extend proximally from the base of internal guide 1950. In this manner, both the internal guide and externally-threaded stem are prevented from rotational movement when advance knob 195 is turned, and thus restricting device locking stem to an appropriate distal or proximal motion along axis 102.

In certain embodiments, the handle portion 110 may include features that provide visual confirmation regarding the integrity of the seal between hemostatic introducer valve 190 and the dilator 159 (or other catheterized instrument) that has been inserted through hemostatic introducer valve 190 and into device lumen 140 of introducer sheath 130. As best shown in FIG. 8A, this may be achieved by way of an opening 1931 in upper housing portion 112, which is situated to the proximal side of steering handle 160 and provides a "window" through which the distal face of hemostatic introducer valve 190 may be viewed. By regularly checking window 1121, the user can readily identify signs (including the leakage of air, blood, or other fluids) that the hemostatic seal between hemostatic introducer valve 190 and a dilator 159 (or other catheter device) has become compromised, and take immediate action to correct the situation. Window 1931 may also allow users to visualize both the rate at which the dilator is being advanced, and the extent to which it has been advanced, and for this purpose the external surface of the dilator (or other instrument for catheterization) may be marked with gradations that can be viewed through window 1931 to provide the user with an indication of the extent to which the dilator (or other instrument for catheterization) has been advanced into (or retracted back through) the introducer sheath.

Certain embodiments of the present invention may include features for improving ultrasonic visualization of the instruments for catheterization that are passed through introducer sheath 130 during procedures. Under identical imaging conditions in a given background medium or tissue, instruments incorporating such features are seen to be qualitatively "brighter" than ultrasound image than instruments without such features, and thus more readily observed during use. This makes it easier for the user to visualize the placement and movement of the instrument, which in turn allows it to be utilized with greater safety and efficacy, particularly when the instruments for catheterization in question have sharp points or edges, or other features that could cause injury during use (for example, as is the case with respect to the beveled point of dilator 150 that is shown in FIGS. 8C and 8D).

In certain embodiments, features for improving ultrasonic visualization may include architectural modifications to the internal and/or external surfaces of instruments for catheterization ("ultrasound visualization modifications") that are utilized in connection with a steerable introducer sheath assembly in accordance with the present disclosure. These ultrasound visualization modifications may include the introduction of one or more depressions or protrusions to the instrument for catheterization at sites for which enhanced visibility is particularly desirable. For example, ultrasound visualization modifications may include one or more punctate depressions or protrusions that generally appear as a cluster of "dots", which may be irregularly scattered, or grouped and arranged in a certain regular configuration. Ultrasound visualization modifications may also include one or more linear grooves or ridges that extend in a perpendicular, parallel, angular, or spiral fashion with respect to the longitudinal center axis of the modified instrument.

In certain embodiments, ultrasound visualization modifications may be exclusively introduced to the interior surfaces of instruments for catheterization that are utilized in connection with a steerable introducer sheath assembly in accordance with an embodiment of the present disclosure. Placing the ultrasound visualization modifications on interior instrument surfaces allows the external instrument surfaces to be kept smooth and free of irregularities, and thereby helps to prevent damage or undesirable alterations to the surrounding tissue that might be caused by external irregularities during the introduction, manipulation, and/or withdrawal of instruments for catheterization having external ultrasound visualization modifications. Limiting ultrasound visualization modifications to interior instrument surfaces likewise prevents such modifications from themselves becoming altered or reduced in effectiveness through contact with potentially-damaging surfaces, and further protects against structural damage or functional inhibition that could sustained by elements of the steerable introducer sheath assembly of the present disclosure because of contact with modified external instrument surfaces (including, for example damage to the introducer sheath and/or the centralized "device" lumen through which the instrument for catheterization is passed).

Figure 10A:
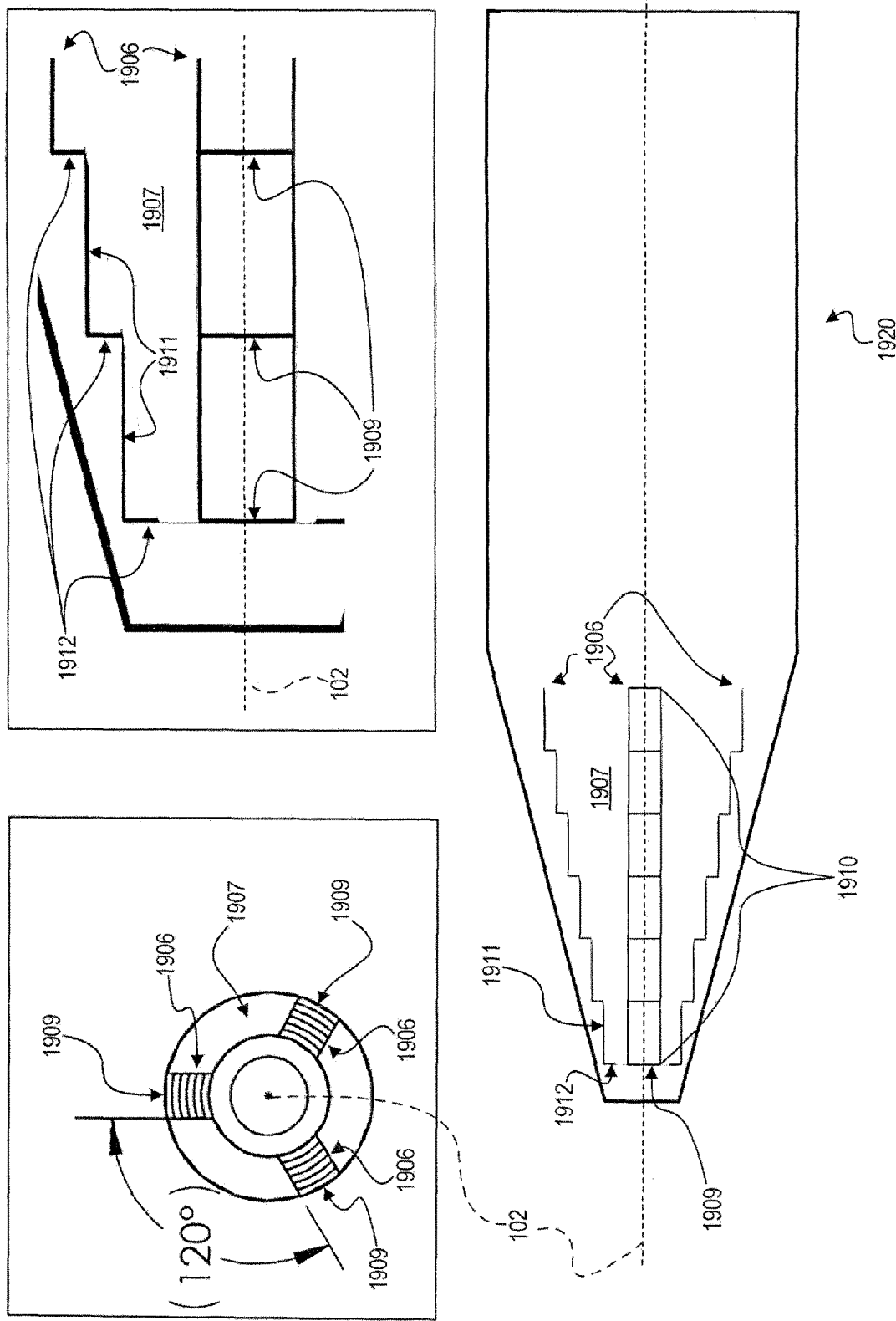
FIG. 10A provides cross-sectional views of a dilator instrument for use with a steerable introducer sheath assembly in accordance with an embodiment of the present disclosure.
Figure 10B:
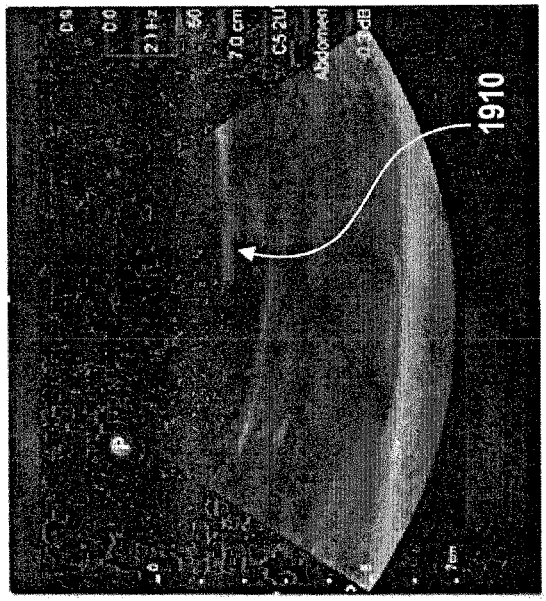
FIG. 10B provides ultrasonic images obtained during introduction (top left) and removal (top right) of a prior art dilator, and ultrasonic images obtained during introduction (bottom left) and removal (bottom right) of a dilator in accordance with an embodiment of the present disclosure.
Figure 10B:
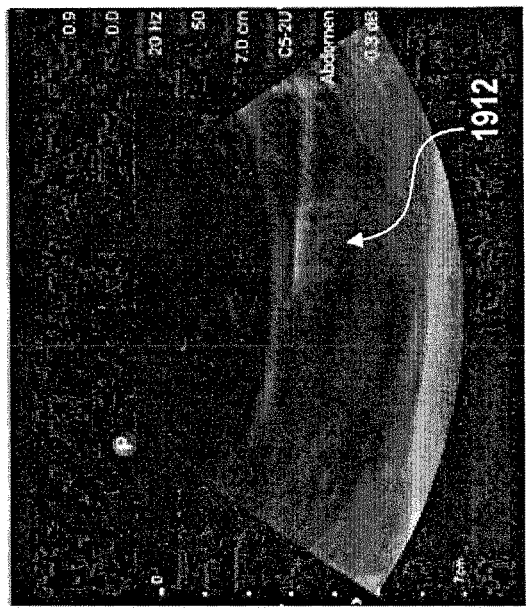
Figure 10B:
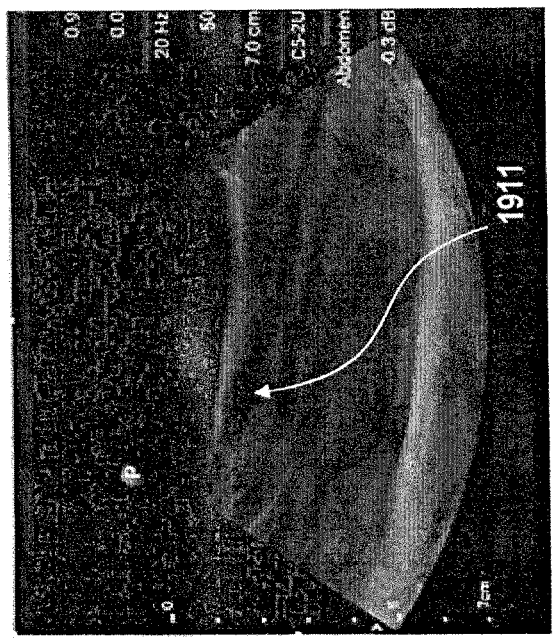
Figure 10B:
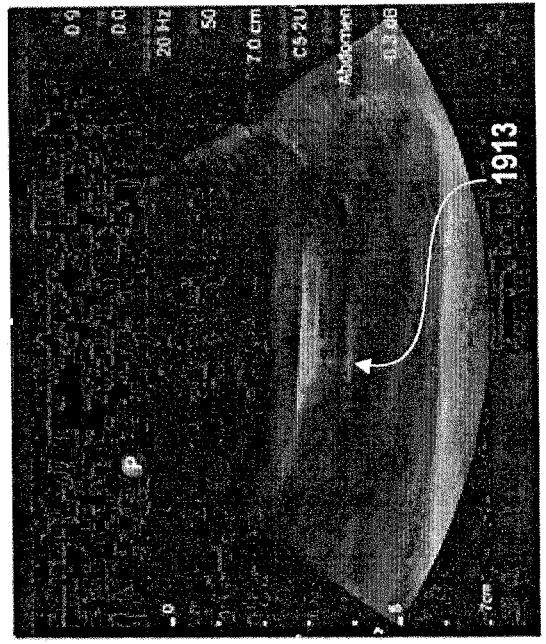

Ultrasound visualization modifications may include any physical or structural alteration to an instrument that causes a subjective or objective improvement in the ultrasonic visibility of the modified instrument in comparison to an unmodified instrument. Subjective improvements may include a "brighter" or otherwise more distinct appearance for a modified instrument that is visualized using ultrasound, when compared to an unmodified instrument visualized under the same conditions. For example, as further discussed below FIG. 10B depicts ultrasonic images of the distal tip of a dilator having improved visualization features in accordance with embodiments of the present disclosure (bottom left and right images), which appear qualitatively "brighter" relative to the distal tip of a prior art dilator (top left and right images) viewed under the same conditions in the same background medium. Given this, a qualitative improvement in the ultrasonic visibility of an instrument with ultrasound visualization modifications according to the present disclosure may be confirmed using any of the known methods for obtaining and analyzing the subjective observations of persons who have examined and compared the subjective appearance of test objects viewed using comparable ultrasonic techniques and conditions (e.g., M. A. McCulloch, et al. *Limitations of Echocardiographic Periarterial Brightness in the Diagnosis of Kawasaki Disease,* 18 JOURNAL OF THE AMERICAN SOCIETY OF ECHOCARDIOGRAPHY 768-770 (2005). For example, a series of ultrasound imaging sessions may be taken of both (i) instruments having ultrasound visualization modifications according to the present disclosure, and (ii) instruments without such modifications, as they are inserted into, manipulation within, and withdrawn from a standardized tissue or test medium. Video clips of these imaging sessions may then be randomly compiled (with any potentially-identifying information removed or obscured), and independently reviewed by technically experienced individuals (e.g., interventional radiologists, ultrasound technicians, cardiologists or other specialist physicians that have experience with using the instrument in question, etc.) who are asked to grade the qualitative "brightness" or "distinctness" of each instrument so imaged. The reviewer grades are collated and processed, and statistical methods such as Cohen's kappa coefficient and the Wilcoxon rank-sum test are applied to confirm whether the instruments with ultrasound visualization modifications appear subjectively "brighter" or more distinct than the instruments without such modifications.

A relative improvement in ultrasound visualization may be also be determined by using known methods for quantifying and comparing the ultrasound signals returned by modified and unmodified instruments, including signal processing and measurement techniques designed to extract information from ultrasound echo signals that are returned from control and test articles. For example, D. Dalecki et al. recently identified and described some exemplary "[h]igh-frequency quantitative ultrasound techniques, including elastography, [that] provide metrics for quantitative assessment of structural, biological, and mechanical properties of engineered constructs" (D. Dalecki et al., *Quantitative Ultrasound for Nondestructive Characterization of Engineered Tissues and Biomaterials,* 44 ANN. BIOMED. ENG'G, 636-648 (2016). The use of such techniques may be further optimized by implementing computer-assisted diagnostic methods, including for example machine-learning algorithms like those used by J. Y. Wu et al. "to train classifiers and label images as normal versus abnormal based on the identified features of the images" (J. Y. Wu, et al., *Quantitative analysis of ultrasound images for computer-aided diagnosis*, 3 J. MED. IMAGING, 014501-1-014501-9 (2016)). To this regard, a number of commercially-available software packages may be used with commercial ultrasound systems to identify, isolate, and quantify a variety of image characteristics. For example, the QLAB Advanced Quantification Software available from Philips Medical Systems may be used in conjunction with commercial ultrasound systems to facilitate the echocardiographic analysis of structure and function (I. S. Salgo, *Clinical benefits of QLAB software for advanced 2D and 3D echo quantification*, Koninklijke Philips Electronics N.V. (2006)).

Given the quantitative tools and methods described above (as well as other quantitative tools and methods that are likewise known in the art), a quantitative improvement in the ultrasonic visibility of an instrument with ultrasound visualization modifications may be confirmed by first obtaining ultrasound imaging sessions of both (i) instruments having ultrasound visualization modifications according to the present disclosure, and (ii) instruments without such modifications, as they are inserted into, manipulation within, and withdrawn from a standardized tissue or test medium. For qualitative analysis, both the video clips of these imaging sessions and the underlying acoustic information that is used to form the image is extracted for analysis by a technically experienced scientist or clinician. For example, the analyst may begin by defining a region of interest (ROI) that contains the portion of the instrument that has received ultrasound visualization modifications, possibly doing so at defined locations within the standardized tissue or test medium, or at pre-defined times (for example, defining one ROI for each of the three phases of the experiment (insertion into, manipulation within the standardized tissue or test medium. Having defined the ROI, the analyst may isolate the acoustic information that underlies the image that is circumscribed by the ROI, using a technique that is known as densitometry. Having thereby isolated the raw acoustic information that underlies ROIs that correspond to the relevant portion of the instrument (i.e. the portion in which ultrasound visualization modifications were either added or not added), and this raw acoustic information may then be processed to provide a quantitative assessment of structural, biological, and mechanical properties of those instruments for catheterization that received ultrasound visualization modifications, and compare them with those instruments for catheterization that did not receive such modifications. These tests are collated and processed, and statistical methods such as Cohen's kappa coefficient and the Wilcoxon rank-sum test are applied as necessary to confirm whether, compared to instruments that do not have ultrasound visualization modifications, the instruments that do have ultrasound visualization modifications are quantitatively "brighter," more distinct, or quantitatively improved with respect to some other visual characteristic that is reflected in the isolated acoustical data.

As noted above, ultrasound visualization modifications may include one or more punctate depressions or protrusions that generally appear as a cluster of "dots", or as one or more linear grooves or ridges that extend in a perpendicular, parallel, angular, or spiral fashion with respect to the longitudinal center axis of the modified instrument for catheterization. Linear grooves for improving ultrasound visualization may be either continuous, or comprised of smaller segments (which themselves may be either joined in a continuous end-to-end fashion, or somewhat separated but still forming a groove that is observably linear). For example, FIG. 10A, depicts a dilator (1920) for catheterization with a steerable introducer sheath assembly of the present disclosure, with said dilator having a distal opening of 0.033 inches, with said opening increasing as the dilator extends in a proximal direction to a maximum internal bore diameter of at least 0.057 inches (note that FIG. 10A provides a representative depiction of dilator 1920 that is not to scale). As shown in FIG. 10A, dilator embodiment (1920) has been modified to improve ultrasound visualization through the introduction of three longitudinal grooves (1906) to the internal bore surface (1907) near the distal tip (1908), with said grooves sited 120 degrees apart from one another in a radial manner about the internal bore (as best shown in FIG. 10A, upper left inset), and extending parallel to each other in a stepped fashion, in a distal-to-proximal direction that is also parallel to longitudinal axis 102 (as best shown in FIG. 10A). Each of the three grooves introduced to dilator 1920 has a groove width (1909) of 0.012 inches and a total groove length (1910) of 0.375 inches, which is further subdivided into six equal steps joined end-to end, with each step having a groove step length (1911) of 0.0625 inches, and a groove step depth (1912) of 0.003 inches (as best shown in FIG. 10A (main body and top right inset).

Inclusion of ultrasound visualization modifications similar to those shown in FIG. 10A facilitates visualization of instruments for catheterization during procedures conducted using ultrasonic imaging. This can be seen in FIG. 10B, which depicts ultrasonic images obtained during the introduction (top left) and removal (top right) of prior art dilators (which do not contain ultrasound visualization modifications), and ultrasonic images obtained during the introduction (bottom left) and removal (bottom right) of the dilator (1920) that is illustrated in FIG. 10A (which includes ultrasound visualization modifications in the form of the stepped grooves that were described above). In comparison to the appearance of the distal dilator tips indicated in FIG. 10B by arrows 1910 and 1911, (from prior art dilators), the appearance of the distal dilator tips indicated by arrows 1912 and 1913 (from the dilator with the "stepped groove" ultrasound visualization modifications depicted in FIG. 10A and discussed herein) shows a marked increase in brilliance, which is observable as a series of parallel "streaks" that extend downward from the apparent position of the distal tip. This increased brilliance in turn facilitates visualization of the dilator's distal tip during procedures conducted using ultrasonic imaging.

In certain embodiments, dilator 159 may also incorporate a barium impregnated polymer that may enhance fluoroscopic visibility of dilators when introduced, for example, using a steerable introducer sheath assembly in accordance with an embodiment of the present disclosure.

What is claimed is:

1. An introducer sheath assembly, characterized by:
    a handle portion including a distal end and a proximal end;
    an introducer sheath extending outwardly from the distal end of the handle portion, the introducer sheath including,
        a device lumen configured to slidably receive a corresponding device,
        at least one steering cable lumen disposed radially outwardly from the device lumen, at least one steering cable that is affixed at a distal end of the introducer sheath, disposed within the at least one steering cable lumen, and engaged with a steering assembly disposed in the handle portion;

one or more steering levers disposed on an outer surface of the handle portion and pivotably affixed to a first end of a steering post, with the steering post having a second end that engages a steering assembly such that rotating the steering lever about a longitudinal axis of the steering post causes the steering assembly to modify the tension in the at least one steering cable; and wherein at least one steering lever engages either directly or indirectly with the surface of the handle portion in a manner that limits an extent to which the steering lever can be rotated about the longitudinal axis of the steering post; and, wherein at least one steering lever is capable of being selectively pivotable positioned in either a locked position in which that steering lever is non-rotatably fixed to the handle portion, or an unlocked position where that steering lever can be rotated relative to the handle portion; and wherein the engagement between the steering lever and handle portion surface that limits the extent to which the steering lever can be rotated can be adjusted by a user to increase or decrease the extent to which the steering lever can be rotated.

2. The introducer sheath assembly of claim 1, further comprising a second steering assembly disposed in the handle configured for attachment of a second steering cable thereto, and a distal cap that engages the second steering assembly such that rotating the distal cap causes the second steering assembly to modify the tension in the second steering cable.

3. The introducer sheath assembly of claim 2, wherein the second steering assembly comprises an externally-threaded stem that passes through a correspondingly-threaded central bore in the distal cap, with the externally-threaded stem being engaged with the proximal end of the second steering cable, wherein the rotation of the distal cap relative to the externally-threaded stem causes the externally-threaded stem to move in either a proximal or distal direction that is parallel to a longitudinal center axis of the handle.

4. The introducer sheath assembly of claim 1, wherein the engagement between the steering lever and the outer surface of the handle portion is mediated by a domed cap that at least partially encompasses the steering lever, with the domed cap being seated in a corresponding-shaped recess in the outer surface of the handle.

5. The introducer sheath assembly of claim 4, wherein a surface of the domed cap contains at least one structural feature that engages with at least one structural feature on the outer surface of the handle portion to limit the extent to which the steering lever can be rotated about the longitudinal axis of its steering post.

6. The introducer sheath assembly of claim 5, wherein at least one of the structural features that limits the extent to which the steering lever can be rotated can be adjusted by a user to increase or decrease the extent to which the steering lever can be rotated about the longitudinal axis.

7. The introducer sheath assembly of claim 1, wherein engagement between at least one steering lever, steering post, and steering assembly is mediated by one or more gears that can be adjusted to modify the extent to which the introducer sheath is displaced from its longitudinal center axis when the steering lever is rotated about the longitudinal axis of its respective steering post.

8. An introducer sheath assembly, characterized by:
a handle portion including a distal end and a proximal end;
an introducer sheath extending outwardly from the distal end of the handle portion, the introducer sheath including,
a device lumen configured to slidably receive a corresponding device,
at least one steering cable lumen disposed radially outwardly from the device lumen, at least one steering cable that is affixed at a distal end of the introducer sheath, disposed within the at least one steering cable lumen, and engaged with a steering assembly disposed in the handle portion;
a steering lever disposed on an outer surface of the handle portion and affixed to a first end of a steering post, with the steering post having a second end that engages a steering assembly such that rotating the steering lever about a longitudinal axis of the steering post causes the steering assembly to modify tension in the at least one steering cable;
wherein at least one steering lever engages either directly or indirectly with the surface of the handle portion in a manner that limits an extent to which the steering lever can be rotated about the longitudinal axis of the steering post; and
wherein the engagement between at least one steering lever, steering post, and steering assembly is mediated by one or more gears that can be adjusted to modify the extent to which the introducer sheath is displaced from its longitudinal center axis when the steering lever is rotated about the longitudinal axis of its respective steering post.

9. The introducer sheath assembly of claim 8, wherein the steering lever is capable of being selectively positioned in either a locked position in which that steering lever is non-rotatably fixed to the handle portion, or an unlocked position where that steering lever can be rotated relative to the handle portion.

10. The introducer sheath assembly of claim 8, further comprising a second steering assembly disposed in the handle configured for attachment of a second steering cable thereto, and a distal cap that engages the second steering assembly such that rotating the distal cap causes the second steering assembly to modify the tension in the second steering cable.

11. The introducer sheath assembly of claim 10, wherein the second steering assembly is an externally-threaded stem that passes through a correspondingly-threaded central bore in the distal cap, with the externally-threaded stem being engaged with the proximal end of, wherein the rotation of the distal cap relative to the externally-threaded stem causes the externally-threaded stem to move in either a proximal or distal direction that is parallel to a longitudinal center axis of the handle.

12. The introducer sheath assembly of claim 8, wherein the engagement between the steering lever and the outer surface of the handle portion is mediated by a domed cap that at least partially encompasses the steering lever, with the domed cap being seated in a corresponding-shaped recess in the outer surface of the handle.

13. The introducer sheath assembly of claim 12, wherein a surface of the domed cap contains at least one structural feature that engages with at least one structural feature on the outer surface of the handle portion to limit the extent to which the steering lever can be rotated about the longitudinal axis of its steering post.

14. The introducer sheath assembly of claim 13, wherein at least one of the structural features that limits the extent to which the steering lever can be rotated can be adjusted by a user to increase or decrease the extent to which the steering lever can be rotated about the longitudinal axis.

15. An introducer sheath assembly, characterized by:
a handle portion including a distal end and a proximal end;
an introducer sheath extending outwardly from the distal end of the handle portion, the introducer sheath including,
a device lumen configured to slidably receive a corresponding device,
a steering cable lumen disposed radially outwardly from the device lumen, a steering cable that is affixed at a distal end of the introducer sheath, disposed within the steering cable lumen, and engaged with a steering assembly disposed in the handle portion;
a steering lever disposed on an outer surface of the handle portion and affixed to a first end of a steering post, with the steering post having a second end that engages a first steering assembly such that rotating the steering lever about a longitudinal axis of the steering post causes the steering assembly to modify tension in the steering cable;
wherein at least one steering lever engages either directly or indirectly with the surface of the handle portion in a manner that limits an extent to which the steering lever can be rotated about the longitudinal axis of the steering post; and
a second steering assembly disposed in the handle configured for attachment of a second steering cable thereto, and
a distal cap that engages the second steering assembly such that rotating the distal cap causes the second steering assembly to modify the tension in the second steering cable.

16. The introducer sheath assembly of claim 15, wherein at least one steering lever is capable of being selectively pivotable positioned in either a locked position in which that steering lever is non-rotatably fixed to the handle portion, or an unlocked position where that steering lever can be rotated relative to the handle portion.

17. The introducer sheath assembly of claim 15, wherein the engagement between at least one steering lever, steering post, and steering assembly is mediated by one or more gears that can be adjusted to modify the extent to which the introducer sheath is displaced from its longitudinal center axis when the steering lever is rotated about the longitudinal axis of its respective steering post.

* * * * *